(12) United States Patent
Titus

(10) Patent No.: US 11,992,374 B2
(45) Date of Patent: May 28, 2024

(54) DEVICE, SYSTEM, AND METHOD FOR DETECTION OF MEDICAL DEVICE COMPONENTS AND/OR MATING THEREOF

(71) Applicant: Becton, Dickinson and Company, Franklin Lakes, NJ (US)

(72) Inventor: Noel Titus, New York, NY (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 17/922,840

(22) PCT Filed: May 6, 2021

(86) PCT No.: PCT/US2021/031031
§ 371 (c)(1),
(2) Date: Nov. 2, 2022

(87) PCT Pub. No.: WO2021/226309
PCT Pub. Date: Nov. 11, 2021

(65) Prior Publication Data
US 2023/0181282 A1    Jun. 15, 2023

Related U.S. Application Data

(60) Provisional application No. 63/021,496, filed on May 7, 2020.

(51) Int. Cl.
*A61B 90/98* (2016.01)
*G06K 19/067* (2006.01)

(52) U.S. Cl.
CPC .......... *A61B 90/98* (2016.02); *G06K 19/0672* (2013.01)

(58) Field of Classification Search
CPC .......... A61B 90/98; A61B 2017/00477; A61B 90/90; G06K 19/0672; G06K 19/0724; G06K 19/07737; G06K 19/07766
See application file for complete search history.

(56) References Cited

U.S. PATENT DOCUMENTS 5,882,338 A    3/1999   Gray
6,366,206 B1   4/2002   Ishikawa et al.
(Continued)

FOREIGN PATENT DOCUMENTS

EP    3388004 A1       10/2018
WO    2006108026 A2    10/2006
WO    2013154919 A2    10/2013

*Primary Examiner* — Tuyen K Vo
(74) *Attorney, Agent, or Firm* — The Webb Law Firm

(57) ABSTRACT

Provided is a medical device assembly for detection of medical device components and/or mating thereof. The medical device assembly may include a first medical device component having at least one first resonant structure, which may have a first resonant frequency spectrum. A second medical device component may have at least one second resonant structure, which may have a second resonant frequency spectrum different than the first resonant frequency spectrum. Upon mating of the first medical device component to the second medical device component, the first resonant structure(s) and the second resonant structure(s) may combine to have a third resonant frequency spectrum, which may be different than the first resonant frequency spectrum and the second resonant frequency spectrum. A system and method are also disclosed.

24 Claims, 16 Drawing Sheets

(56) References Cited

U.S. PATENT DOCUMENTS

| | | | |
|---|---|---|---|
| 7,883,534 B1* | 2/2011 | Crosby | A61N 5/0613 607/90 |
| 8,120,485 B2 | 2/2012 | Yang | |
| 8,328,082 B1 | 12/2012 | Bochenko et al. | |
| 8,961,441 B2 | 2/2015 | Cioanta et al. | |
| 10,784,839 B2* | 9/2020 | Kim | H03H 9/54 |
| 10,874,480 B2* | 12/2020 | Mangelberger | A61B 90/90 |
| 2002/0032435 A1 | 3/2002 | Levin | |
| 2002/0154029 A1* | 10/2002 | Watters | G01D 5/48 340/870.07 |
| 2005/0154368 A1 | 7/2005 | Lim et al. | |
| 2006/0135843 A1 | 6/2006 | Heath | |
| 2006/0196936 A1 | 9/2006 | Christofferson et al. | |
| 2006/0224128 A1 | 10/2006 | Lurvey et al. | |
| 2007/0179448 A1 | 8/2007 | Lim et al. | |
| 2014/0364775 A1 | 12/2014 | Du et al. | |
| 2015/0116126 A1* | 4/2015 | Hyde | G01D 4/02 340/870.02 |
| 2015/0119652 A1* | 4/2015 | Hyde | A61B 5/02055 604/290 |
| 2015/0120312 A1* | 4/2015 | Hyde | G16H 40/67 705/2 |
| 2015/0215705 A1* | 7/2015 | Kang | H04R 17/00 381/190 |
| 2016/0148027 A1* | 5/2016 | Schoutens | G06K 19/07749 340/10.1 |
| 2016/0217259 A1* | 7/2016 | Chan | G16H 50/20 |
| 2016/0254842 A1* | 9/2016 | Hong | H01Q 1/36 343/867 |
| 2016/0374744 A1* | 12/2016 | Akagane | A61B 18/14 606/27 |
| 2017/0016838 A1* | 1/2017 | Donohue | G01N 22/04 |
| 2018/0225560 A1* | 8/2018 | Schneider | A61M 5/5086 |
| 2019/0242528 A1* | 8/2019 | Frenal | F17C 13/04 |
| 2020/0261654 A1* | 8/2020 | Kühni | A61M 5/20 |
| 2022/0154029 A1* | 5/2022 | Greenwood | C09D 7/62 |

* cited by examiner

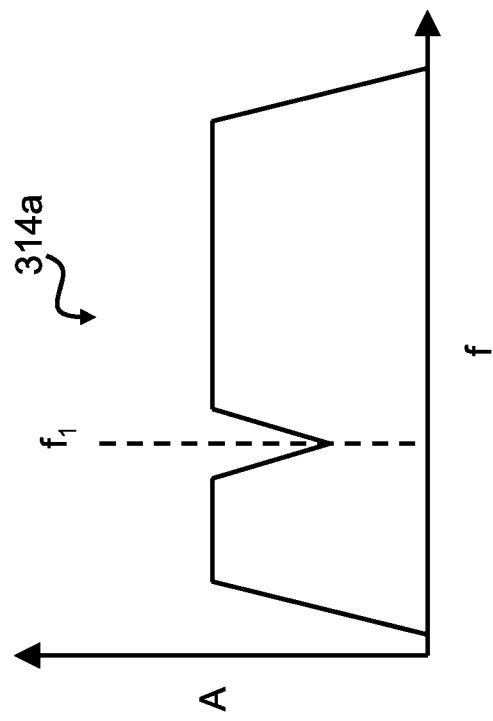
FIG. 3B
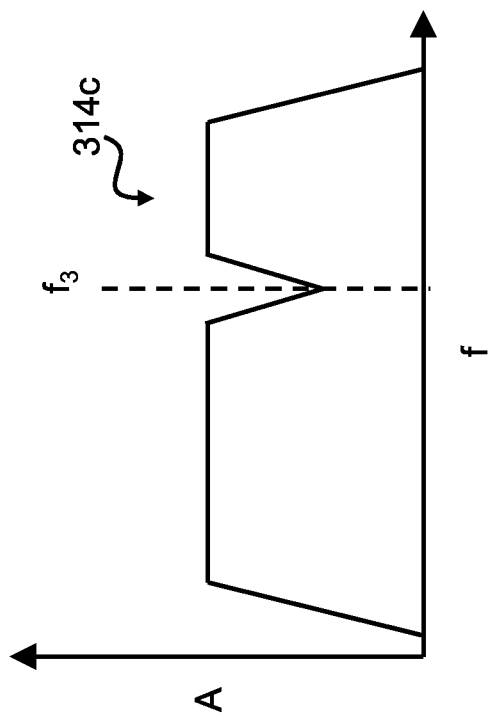
FIG. 3D
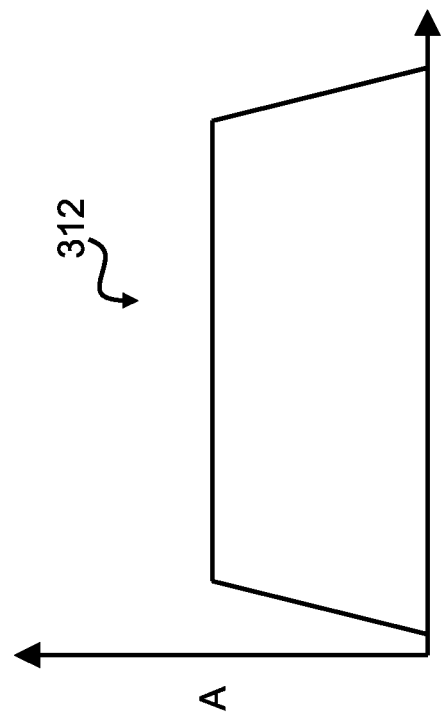
FIG. 3A
FIG. 3C

DEVICE, SYSTEM, AND METHOD FOR DETECTION OF MEDICAL DEVICE COMPONENTS AND/OR MATING THEREOF

CROSS-REFERENCE TO RELATED APPLICATIONS

This application is the United States national phase of International Application No. PCT/US2021/031031 filed May 6, 2021, and claims priority to U.S. Provisional Application Ser. No. 63/021,496, filed May 7, 2020, entitled Device, System, and Method for Detection of Medical Device Components and/or Mating Thereof, the entire disclosures of which are hereby incorporated by reference in their entirety.

BACKGROUND

1. Field

This disclosed subject matter relates generally to devices, systems, and methods for detecting medical device components and, in some particular embodiments or aspects, to a device, system, and method for detection of mating of medical device components.

2. Technical Considerations

Certain techniques for identifying products may include machine-readable optical labels (e.g., barcodes, quick response (QR) codes, and/or the like). For example, optical labels may be relatively inexpensive to fix to a product and/or the packaging thereof (e.g., by affixing a sticker to the product and/or packaging, by printing directly on the product and/or packaging, and/or the like). However, readers of such optical labels may use a relatively complex optical system, may require line of sight (e.g., between the reader and the optical label) for operation, may need to be manually aligned and/or triggered, may be difficult to use in automation, and/or the like.

Other techniques for identifying products may include radio frequency identification (RFID) tags. For example, such RFID tags may include an application specific integrated circuit (ASIC) and an antenna. The antenna may allow for transmitting and/or receiving of data via radio communication, which may not require line of sight for operation. The ASIC may allow for storing data on, reading data from, and/or writing data to the RFID tag. However, such RFID tags may be relatively expensive, which may be at least partially attributable to the cost and/or time to produce the ASIC. Additionally, while the ability to operate without line of sight may be preferable for automation, the increased cost of RFID tags (e.g., compared to optical labels) may be unsuitable (e.g., for manufacturing, identification, tracking, and/or the like of inexpensive and/or disposable products, such as inexpensive and/or disposable medical device components).

Additionally, while certain techniques (e.g., optical labels, RFID tags, or the like) may be used to identify individual products, such techniques may be incapable of detecting mating of products (e.g., mating of medical device components).

SUMMARY

Accordingly, it is an object of the presently disclosed subject matter to provide devices, systems, and methods for detecting medical device components and/or mating thereof.

According to non-limiting embodiments or aspects, provided is a medical device assembly for detecting medical device components and/or mating thereof. In some non-limiting embodiments or aspects, a medical device assembly for detecting medical device components and/or mating thereof may include a first medical device component having at least one first resonant structure. The first resonant structure(s) may have a first resonant frequency spectrum. A second medical device component may have at least one second resonant structure. The second resonant structure(s) may have a second resonant frequency spectrum different than the first resonant frequency spectrum. Upon mating of the first medical device component to the second medical device component, the first resonant structure(s) and the second resonant structure(s) may combine to have a third resonant frequency spectrum. The third resonant frequency spectrum may be different than the first resonant frequency spectrum and the second resonant frequency spectrum.

In some non-limiting embodiments or aspects, the first resonant structure(s) may include a first spiral resonator. Additionally or alternatively, the first resonant frequency spectrum may include a first natural frequency of the first spiral resonator. In some non-limiting embodiments or aspects, the second resonant structure(s) may include a second spiral resonator. Additionally or alternatively, the second resonant frequency spectrum may include a second natural frequency of the second spiral resonator. In some non-limiting embodiments or aspects, upon mating of the first medical device component to the second medical device component, the first spiral resonator and the second spiral resonator may be coupled to form a resonant circuit having a third natural frequency. Additionally or alternatively, the third resonant frequency spectrum may include the third natural frequency of the resonant circuit.

In some non-limiting embodiments or aspects, the first spiral resonator may include a first spiral-shaped metallic conductor adjacent to a first metallic strip of at least one first antenna element of the first medical device component. Additionally or alternatively, the first spiral-shaped metallic conductor may have a first inductance, a first capacitance, a first resistance, any combination thereof, and/or the like. In some non-limiting embodiments or aspects, the second spiral resonator may include a second spiral-shaped metallic conductor adjacent to a second metallic strip of at least one second antenna element of the second medical device component. Additionally or alternatively, the second spiral-shaped metallic conductor may have a second inductance, a second capacitance, a second resistance, any combination thereof, and/or the like. In some non-limiting embodiments or aspects, at least one of the first inductance, first capacitance, and/or first resistance may be different than at least one of the second inductance, second capacitance, and/or second resistance, respectively.

In some non-limiting embodiments or aspects, the first medical device component may include a male luer fitting and/or the second medical device component may include a corresponding female luer fitting. Additionally or alternatively, the first resonant structure(s) may be disposed with the male luer fitting and the second resonant structure may be disposed with the female luer fitting.

In some non-limiting embodiments or aspects, the first resonant structure(s) may include a plurality of first resonant structures. Additionally or alternatively, each of the plurality of first resonant structures may be positioned at a distinct scale marking on the first medical device component. In some non-limiting embodiments or aspects, each of the plurality of first resonant structures may include a conductive ink.

In some non-limiting embodiments or aspects, the first medical device component may include a first receiving antenna element and a first transmitting antenna element. Additionally or alternatively, the first receiving antenna element and the first transmitting antenna element may be cross-polarized. In some non-limiting embodiments or aspects, the second medical device component may include a second receiving antenna element and a second transmitting antenna element. Additionally or alternatively, the second receiving antenna element and the second transmitting antenna element may be cross-polarized.

In some non-limiting embodiments or aspects, upon interrogation of the first medical device component with a multi-frequency electromagnetic signal, the first resonant structure(s) may attenuate at least one first frequency component of the multi-frequency electromagnetic signal corresponding to the first resonant frequency spectrum to form a first attenuated electromagnetic signal. Additionally or alternatively, upon interrogation of the second medical device component with the multi-frequency electromagnetic signal, the second resonant structure(s) may attenuate at least one second frequency component of the multi-frequency electromagnetic signal corresponding to the second resonant frequency spectrum to form a second attenuated electromagnetic signal. In some non-limiting embodiments or aspects, upon interrogation of the first medical device component mated with the second medical device component with the multi-frequency electromagnetic signal, at least one third frequency component of the multi-frequency electromagnetic signal corresponding to the third resonant frequency spectrum may be attenuated to form a third attenuated electromagnetic signal.

In some non-limiting embodiments or aspects, the multi-frequency electromagnetic signal may be generated by a first generator. Additionally or alternatively, at least one of the first attenuated electromagnetic signal, the second attenuated electromagnetic signal, and/or the third attenuated electromagnetic signal may be detected by a first reader.

According to non-limiting embodiments or aspects, provided is a system for detecting medical device components and/or mating thereof. In some non-limiting embodiments or aspects, a system for detecting medical device components and/or mating thereof may include a medical device assembly, which may include a first medical device component and a second medical device component. The first medical device component may have at least one first resonant structure, which may have a first resonant frequency spectrum. The second medical device component may have at least one second resonant structure, which may have a second resonant frequency spectrum different than the first resonant frequency spectrum. Upon mating of the first medical device component to the second medical device component, the first resonant structure(s) and the second resonant structure(s) may combine to have a third resonant frequency spectrum, which may be different than the first resonant frequency spectrum and the second resonant frequency spectrum. At least one generator may transmit an interrogation signal to the medical device assembly. At least one reader may receive at least one reflected signal from the medical device assembly.

In some non-limiting embodiments or aspects, the interrogation signal may include a multi-frequency electromagnetic signal. Additionally or alternatively, the interrogation signal may include a continuous wave, multi-frequency electromagnetic signal of uniform amplitude and phase.

In some non-limiting embodiments or aspects, upon interrogation of the first medical device component with the multi-frequency electromagnetic signal, the first resonant structure(s) may attenuate at least one first frequency component of the multi-frequency electromagnetic signal corresponding to the first resonant frequency spectrum to form a first attenuated electromagnetic signal. Additionally or alternatively, upon interrogation of the second medical device component with the multi-frequency electromagnetic signal, the second resonant structure(s) may attenuate at least one second frequency component of the multi-frequency electromagnetic signal corresponding to the second resonant frequency spectrum to form a second attenuated electromagnetic signal. In some non-limiting embodiments or aspects, upon interrogation of the first medical device component mated with the second medical device component with the multi-frequency electromagnetic signal, at least one third frequency component of the multi-frequency electromagnetic signal corresponding to the third resonant frequency spectrum may be attenuated to form a third attenuated electromagnetic signal. In some non-limiting embodiments or aspects, the reflected signal(s) may include at least one of the first attenuated electromagnetic signal, the second attenuated electromagnetic signal, and/or the third attenuated electromagnetic signal.

In some non-limiting embodiments or aspects, upon interrogation of the first medical device component with the interrogation signal, the reader(s) may detect the first resonant frequency spectrum by at least one of an amplitude attenuation, a phase jump, a frequency attenuation, any combination thereof, and/or the like in the reflected signal(s) corresponding to the first resonant frequency spectrum. Additionally or alternatively, upon interrogation of the second medical device component with the interrogation signal, the reader(s) may detect the second resonant frequency spectrum by at least one of an amplitude attenuation, a phase jump, a frequency attenuation, any combination thereof, and/or the like in the reflected signal(s) corresponding to the second resonant frequency spectrum. In some non-limiting embodiments or aspects, upon interrogation of the first medical device component mated with the second medical device component with the interrogation signal, the reader(s) may detects the third resonant frequency spectrum by at least one of an amplitude attenuation, a phase jump, a frequency attenuation, any combination thereof, and/or the like in the at least one reflected signal corresponding to the third resonant frequency spectrum.

In some non-limiting embodiments or aspects, the reader(s) may include a first communication interface to communicate reflected signal data associated with the reflected signal over a first network. Additionally or alternatively, at least one server may have a second communication interface configured to communicate with the first communication interface of the at least one reader over the first network. In some non-limiting embodiments or aspects, the server(s) may receive the reflected signal data over the first network. Additionally or alternatively, the server(s) may store the reflected signal data in a database.

In some non-limiting embodiments or aspects, the at least one reader may include a plurality of readers. Additionally or alternatively, each reader may be at a location within at least one site, and the location of each reader may be different than the location of all other readers of the plurality of readers. In some non-limiting embodiments or aspects, a location of the medical device assembly may be determined based on which reader of the plurality of readers detects the medical device assembly.

In some non-limiting embodiments or aspects, the first resonant structure(s) may include a first spiral resonator. Additionally or alternatively, the first resonant frequency spectrum may include a first natural frequency of the first spiral resonator. In some non-limiting embodiments or aspects, the second resonant structure(s) may include a second spiral resonator. Additionally or alternatively, the second resonant frequency spectrum may include a second natural frequency of the second spiral resonator. In some non-limiting embodiments or aspects, upon mating of the first medical device component to the second medical device component, the first spiral resonator and the second spiral resonator may be coupled to form a resonant circuit having a third natural frequency. Additionally or alternatively, the third resonant frequency spectrum may include the third natural frequency of the resonant circuit.

In some non-limiting embodiments or aspects, the first medical device component may include a male luer fitting and the second medical device component may include a corresponding female luer fitting. Additionally or alternatively, the first resonant structure(s) may be disposed with the male luer fitting and the second resonant structure(s) may be disposed with the female luer fitting.

In some non-limiting embodiments or aspects, the first resonant structure(s) may include a plurality of first resonant structures. Additionally or alternatively, each of the plurality of first resonant structures may be positioned at a distinct scale marking on the first medical device component. In some non-limiting embodiments or aspects, each of the plurality of first resonant structures may include a conductive ink.

In some non-limiting embodiments or aspects, the first medical device component may include at least one first antenna element. Additionally or alternatively, the second medical device component may include at least one second antenna element. In some non-limiting embodiments or aspects, the generator may include at least one third antenna element. Additionally or alternatively, the reader may include at least one fourth antenna element. In some non-limiting embodiments or aspects, the generator may transmit the interrogation signal with the third antenna element(s) and the reader may receive the reflected signal with the fourth antenna element(s). Additionally or alternatively, the interrogation signal may be received by at least one of the first antenna element(s), the second antenna element(s), any combination thereof, and/or the like. Additionally or alternatively, the reflected signal may be transmitted by at least one of the first antenna element(s), the second antenna element(s), any combination thereof, and/or the like.

According to non-limiting embodiments or aspects, provided is a method for detecting mating of medical device components. In some non-limiting embodiments or aspects, a method for detecting mating of medical device components may include providing a first medical device component having at least one first resonant structure. The first resonant structure(s) may have a first resonant frequency spectrum. A second medical device component having at least one second resonant structure may be provided. The second resonant structure(s) may have a second resonant frequency spectrum different than the first resonant frequency spectrum. The first medical device component may be mated to the second medical device component to form a medical device assembly. Upon mating, the first resonant structure(s) and the second resonant structure(s) may combine to have a third resonant frequency spectrum. The third resonant frequency spectrum may be different than the first resonant frequency spectrum and the second resonant frequency spectrum. The medical device assembly may be interrogated with an interrogation signal. Additionally or alternatively, a reflected signal from the medical device assembly may be detected. The reflected signal may correspond to the third resonant frequency spectrum.

In some non-limiting embodiments or aspects, the interrogation signal may include a multi-frequency electromagnetic signal.

In some non-limiting embodiments or aspects, upon interrogation of the medical device assembly with the interrogation signal, at least one frequency component of the interrogation signal corresponding to the third resonant frequency spectrum may be attenuated to form the reflected signal. In some non-limiting embodiments or aspects, detecting the reflected signal may include receiving the reflected signal and detecting at least one of an amplitude attenuation, a phase jump, a frequency attenuation, any combination thereof, and/or the like in the reflected signal corresponding to the third resonant frequency spectrum.

In some non-limiting embodiments or aspects, reflected signal data associated with the reflected signal may be stored in a database.

In some non-limiting embodiments or aspects, detecting the reflected signal may include detecting the reflected signal with a reader. In some non-limiting embodiments or aspects, the reader may be one of a plurality of readers. Additionally or alternatively, each reader of the plurality of readers may be at a location within at least one site. In some non-limiting embodiments or aspects, a location of the medical device assembly may be determined based on the location of the reader.

In some non-limiting embodiments or aspects, the first resonant structure(s) may include a first spiral resonator. Additionally or alternatively, the first resonant frequency spectrum may include a first natural frequency of the first spiral resonator. In some non-limiting embodiments or aspects, the second resonant structure(s) may include a second spiral resonator. Additionally or alternatively, the second resonant frequency spectrum may include a second natural frequency of the second spiral resonator. In some non-limiting embodiments or aspects, upon mating of the first medical device component to the second medical device component, the first spiral resonator and the second spiral resonator may be coupled to form a resonant circuit having a third natural frequency. Additionally or alternatively, the third resonant frequency spectrum may include the third natural frequency of the resonant circuit.

In some non-limiting embodiments or aspects, the first medical device component may include a male luer fitting. Additionally or alternatively, the second medical device component may include a corresponding female luer fitting. In some non-limiting embodiments or aspects, the first resonant structure(s) may be disposed with the male luer fitting. Additionally or alternatively, the second resonant structure(s) may be disposed with the female luer fitting.

In some non-limiting embodiments or aspects, the first resonant structure(s) may include a plurality of first resonant structures. Additionally or alternatively, each of the plurality of first resonant structures may be positioned at a distinct scale marking on the first medical device component. In some non-limiting embodiments or aspects, each of the plurality of first resonant structures may include a conductive ink.

Further embodiments or aspects are set forth in the following numbered clauses:

Clause 1: A medical device assembly, comprising: a first medical device component having at least one first resonant structure, the at least one first resonant structure having a first resonant frequency spectrum; and a second medical device component having at least one second resonant structure, the at least one second resonant structure having a second resonant frequency spectrum different than the first resonant frequency spectrum, wherein, upon mating of the first medical device component to the second medical device component, the at least one first resonant structure and the at least one second resonant structure combine to have a third resonant frequency spectrum, wherein the third resonant frequency spectrum is different than the first resonant frequency spectrum and the second resonant frequency spectrum.

Clause 2: The medical device assembly of clause 1, wherein the at least one first resonant structure comprises a first spiral resonator, wherein the first resonant frequency spectrum comprises a first natural frequency of the first spiral resonator, wherein the at least one second resonant structure comprises a second spiral resonator, and wherein the second resonant frequency spectrum comprises a second natural frequency of the second spiral resonator.

Clause 3. The medical device assembly of any preceding clause, wherein, upon mating of the first medical device component to the second medical device component, the first spiral resonator and the second spiral resonator are coupled to form a resonant circuit having a third natural frequency, and wherein the third resonant frequency spectrum comprises the third natural frequency of the resonant circuit.

Clause 4. The medical device assembly of any preceding clause, wherein the first spiral resonator comprises a first spiral-shaped metallic conductor adjacent to a first metallic strip of at least one first antenna element of the first medical device component, the first spiral-shaped metallic conductor having a first inductance, a first capacitance, and a first resistance, and wherein the second spiral resonator comprises a second spiral-shaped metallic conductor adjacent to a second metallic strip of at least one second antenna element of the second medical device component, the second spiral-shaped metallic conductor having a second inductance, a second capacitance, and a second resistance, wherein at least one of the first inductance, first capacitance, or first resistance is different than at least one of the second inductance, second capacitance, or second resistance, respectively.

Clause 5. The medical device assembly of any preceding clause, wherein the first medical device component comprises a male luer fitting and the second medical device component comprises a corresponding female luer fitting, and wherein the at least one first resonant structure is disposed with the male luer fitting and the at least one second resonant structure is disposed with the female luer fitting.

Clause 6. The medical device assembly of any preceding clause, wherein the at least one first resonant structure comprises a plurality of first resonant structures, each of the plurality of first resonant structures positioned at a distinct scale marking on the first medical device component, and wherein each of the plurality of first resonant structures comprises a conductive ink.

Clause 7. The medical device assembly of any preceding clause, wherein the first medical device component comprises a first receiving antenna element and a first transmitting antenna element, wherein the first receiving antenna element and the first transmitting antenna element are cross-polarized, wherein the second medical device component comprises a second receiving antenna element and a second transmitting antenna element, and wherein the second receiving antenna element and the second transmitting antenna element are cross-polarized.

Clause 8. The medical device assembly of any preceding clause, wherein, upon interrogation of the first medical device component with a multi-frequency electromagnetic signal, the at least one first resonant structure attenuates at least one first frequency component of the multi-frequency electromagnetic signal corresponding to the first resonant frequency spectrum to form a first attenuated electromagnetic signal, wherein, upon interrogation of the second medical device component with the multi-frequency electromagnetic signal, the at least one second resonant structure attenuates at least one second frequency component of the multi-frequency electromagnetic signal corresponding to the second resonant frequency spectrum to form a second attenuated electromagnetic signal, and wherein, upon interrogation of the first medical device component mated with the second medical device component with the multi-frequency electromagnetic signal, at least one third frequency component of the multi-frequency electromagnetic signal corresponding to the third resonant frequency spectrum is attenuated to form a third attenuated electromagnetic signal.

Clause 9. The medical device assembly of any preceding clause, wherein the multi-frequency electromagnetic signal is generated by a first generator, and wherein at least one of the first attenuated electromagnetic signal, the second attenuated electromagnetic signal, or the third attenuated electromagnetic signal are detected by a first reader.

Clause 10. A system, comprising: a medical device assembly, comprising: a first medical device component having at least one first resonant structure, the at least one first resonant structure having a first resonant frequency spectrum; and a second medical device component having at least one second resonant structure, the at least one second resonant structure having a second resonant frequency spectrum different than the first resonant frequency spectrum, wherein, upon mating of the first medical device component to the second medical device component, the at least one first resonant structure and the at least one second resonant structure combine to have a third resonant frequency spectrum, wherein the third resonant frequency spectrum is different than the first resonant frequency spectrum and the second resonant frequency spectrum; at least one generator configured to transmit an interrogation signal to the medical device assembly; and at least one reader configured to receive at least one reflected signal from the medical device assembly.

Clause 11. The system of clause 10, wherein the interrogation signal comprises a multi-frequency electromagnetic signal.

Clause 12. The system of clauses 10 or 11, wherein the interrogation signal comprises a continuous wave, multi-frequency electromagnetic signal of uniform amplitude and phase.

Clause 13. The system of any one of clauses 10-12, wherein, upon interrogation of the first medical device component with the multi-frequency electromagnetic signal, the at least one first resonant structure attenuates at least one first frequency component of the multi-frequency electromagnetic signal corresponding to the first resonant frequency spectrum to form a first attenuated electromagnetic signal, wherein, upon interrogation of the second medical device component with the multi-frequency electromagnetic signal, the at least one second resonant structure attenuates at least one second frequency component of the multi-frequency electromagnetic signal corresponding to the second resonant frequency spectrum to form a second attenuated electromagnetic signal, wherein, upon interrogation of the first medical device component mated with the second medical device component with the multi-frequency electromagnetic signal, at least one third frequency component of the multi-frequency electromagnetic signal corresponding to the third resonant frequency spectrum is attenuated to form a third attenuated electromagnetic signal, and wherein the at least one reflected signal comprises at least one of the first attenuated electromagnetic signal, the second attenuated electromagnetic signal, or the third attenuated electromagnetic signal.

Clause 14. The system of any one of clauses 10-13, wherein, upon interrogation of the first medical device component with the interrogation signal, the at least one reader detects the first resonant frequency spectrum by at least one of an amplitude attenuation, a phase jump, or a frequency attenuation in the at least one reflected signal corresponding to the first resonant frequency spectrum, wherein, upon interrogation of the second medical device component with the interrogation signal, the at least one reader detects the second resonant frequency spectrum by at least one of an amplitude attenuation, a phase jump, or a frequency attenuation in the at least one reflected signal corresponding to the second resonant frequency spectrum, and wherein, upon interrogation of the first medical device component mated with the second medical device component with the interrogation signal, the at least one reader detects the third resonant frequency spectrum by at least one of an amplitude attenuation, a phase jump, or a frequency attenuation in the at least one reflected signal corresponding to the third resonant frequency spectrum.

Clause 15. The system of any one of clauses 10-14, wherein the at least one reader further comprises a first communication interface to communicate reflected signal data associated with the reflected signal over a first network, the system further comprising: at least one server having a second communication interface configured to communicate with the first communication interface of the at least one reader over the first network, wherein the at least one server is configured to receive the reflected signal data over the first network, and wherein the at least one server is configured to store the reflected signal data in a database.

Clause 16. The system of any one of clauses 10-15, wherein the at least one reader comprises a plurality of readers, each reader of the plurality of readers at a location within at least one site, wherein the location of each reader of the plurality of readers is different than the location of all other readers of the plurality of readers.

Clause 17. The system of any one of clauses 10-16, wherein a location of the medical device assembly is determined based on which reader of the plurality of readers detects the medical device assembly.

Clause 18. The system of any one of clauses 10-17, wherein the at least one first resonant structure comprises a first spiral resonator, wherein the first resonant frequency spectrum comprises a first natural frequency of the first spiral resonator, wherein the at least one second resonant structure comprises a second spiral resonator, and wherein the second resonant frequency spectrum comprises a second natural frequency of the second spiral resonator.

Clause 19. The system of any one of clauses 10-18, wherein, upon mating of the first medical device component to the second medical device component, the first spiral resonator and the second spiral resonator are coupled to form a resonant circuit having a third natural frequency, and wherein the third resonant frequency spectrum comprises the third natural frequency of the resonant circuit.

Clause 20. The system of any one of clauses 10-19, wherein the first medical device component comprises a male luer fitting and the second medical device component comprises a corresponding female luer fitting, and wherein the at least one first resonant structure is disposed with the male luer fitting and the at least one second resonant structure is disposed with the female luer fitting.

Clause 21. The system of any one of clauses 10-20, wherein the at least one first resonant structure comprises a plurality of first resonant structures, each of the plurality of first resonant structures positioned at a distinct scale marking on the first medical device component, and wherein each of the plurality of first resonant structures comprises a conductive ink.

Clause 22. The system of any one of clauses 10-21, wherein the first medical device component comprises at least one first antenna element, the second medical device component comprises at least one second antenna element, the generator comprises at least one third antenna element, and the reader comprises at least one fourth antenna element, wherein the generator is configured to transmit the interrogation signal with the at least one third antenna element and the reader is configured to receive the reflected signal with the at least one fourth antenna element, wherein the interrogation signal is received by at least one of the at least one first antenna element or the at least one second antenna element, and wherein the reflected signal is transmitted by at least one of the at least one first antenna element or the at least one second antenna element.

Clause 23. A method for detecting mating of medical device components, comprising: providing a first medical device component having at least one first resonant structure, the at least one first resonant structure having a first resonant frequency spectrum; providing a second medical device component having at least one second resonant structure, the at least one second resonant structure having a second resonant frequency spectrum different than the first resonant frequency spectrum; mating the first medical device component to the second medical device component to form a medical device assembly, wherein, upon mating, the at least one first resonant structure and the at least one second resonant structure combine to have a third resonant frequency spectrum, the third resonant frequency spectrum being different than the first resonant frequency spectrum and the second resonant frequency spectrum; interrogating the medical device assembly with an interrogation signal; and detecting a reflected signal from the medical device assembly, the reflected signal corresponding to the third resonant frequency spectrum.

Clause 24. The method of clause 23, wherein the interrogation signal comprises a multi-frequency electromagnetic signal.

Clause 25. The method of clauses 23 or 24, wherein, upon interrogation of the medical device assembly with the interrogation signal, at least one frequency component of the interrogation signal corresponding to the third resonant frequency spectrum is attenuated to form the reflected signal.

Clause 26. The method of any one of clauses 23-25, wherein detecting the reflected signal comprises receiving the reflected signal and detecting at least one of an amplitude attenuation, a phase jump, or a frequency attenuation in the reflected signal corresponding to the third resonant frequency spectrum.

Clause 27. The method of any one of clauses 23-26, further comprising storing reflected signal data associated with the reflected signal in a database.

Clause 28. The method of any one of clauses 23-27, wherein detecting the reflected signal comprises detecting the reflected signal with a reader, wherein the reader is one of a plurality of readers, each reader of the plurality of readers at a location within at least one site, the method further comprising: determining a location of the medical device assembly based on the location of the reader.

Clause 29. The method of any one of clauses 23-28, wherein the at least one first resonant structure comprises a first spiral resonator, wherein the first resonant frequency spectrum comprises a first natural frequency of the first spiral resonator, wherein the at least one second resonant structure comprises a second spiral resonator, wherein the second resonant frequency spectrum comprises a second natural frequency of the second spiral resonator, wherein, upon mating of the first medical device component to the second medical device component, the first spiral resonator and the second spiral resonator are coupled to form a resonant circuit having a third natural frequency, and wherein the third resonant frequency spectrum comprises the third natural frequency of the resonant circuit.

Clause 30. The method of any one of clauses 23-29, wherein the first medical device component comprises a male luer fitting and the second medical device component comprises a corresponding female luer fitting, and wherein the at least one first resonant structure is disposed with the male luer fitting and the at least one second resonant structure is disposed with the female luer fitting.

Clause 31. The method of any one of clauses 23-30, wherein the at least one first resonant structure comprises a plurality of first resonant structures, each of the plurality of first resonant structures positioned at a distinct scale marking on the first medical device component, and wherein each of the plurality of first resonant structures comprises a conductive ink.

These and other features and characteristics of the presently disclosed subject matter, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosed subject matter. As used in the specification and the claims, the singular form of "a," "an," and "the" include plural referents unless the context clearly dictates otherwise.

BRIEF DESCRIPTION OF THE DRAWINGS

Additional advantages and details of the disclosed subject matter are explained in greater detail below with reference to the exemplary embodiments or aspects that are illustrated in the accompanying figures, in which:

FIG. 3A is a graph of a non-limiting embodiment or aspect of frequency spectra of an implementation of one or more systems and/or one or more devices of FIG. 1 according to the principles of the presently disclosed subject matter;

FIG. 3B is a graph of a non-limiting embodiment or aspect of frequency spectra of an implementation of one or more systems and/or one or more devices of FIG. 1 according to the principles of the presently disclosed subject matter;

FIG. 3C is a graph of a non-limiting embodiment or aspect of frequency spectra of an implementation of one or more systems and/or one or more devices of FIG. 1 according to the principles of the presently disclosed subject matter;

FIG. 3D is a graph of a non-limiting embodiment or aspect of frequency spectra of an implementation of one or more systems and/or one or more devices of FIG. 1 according to the principles of the presently disclosed subject matter;

DESCRIPTION

Figure 1A:
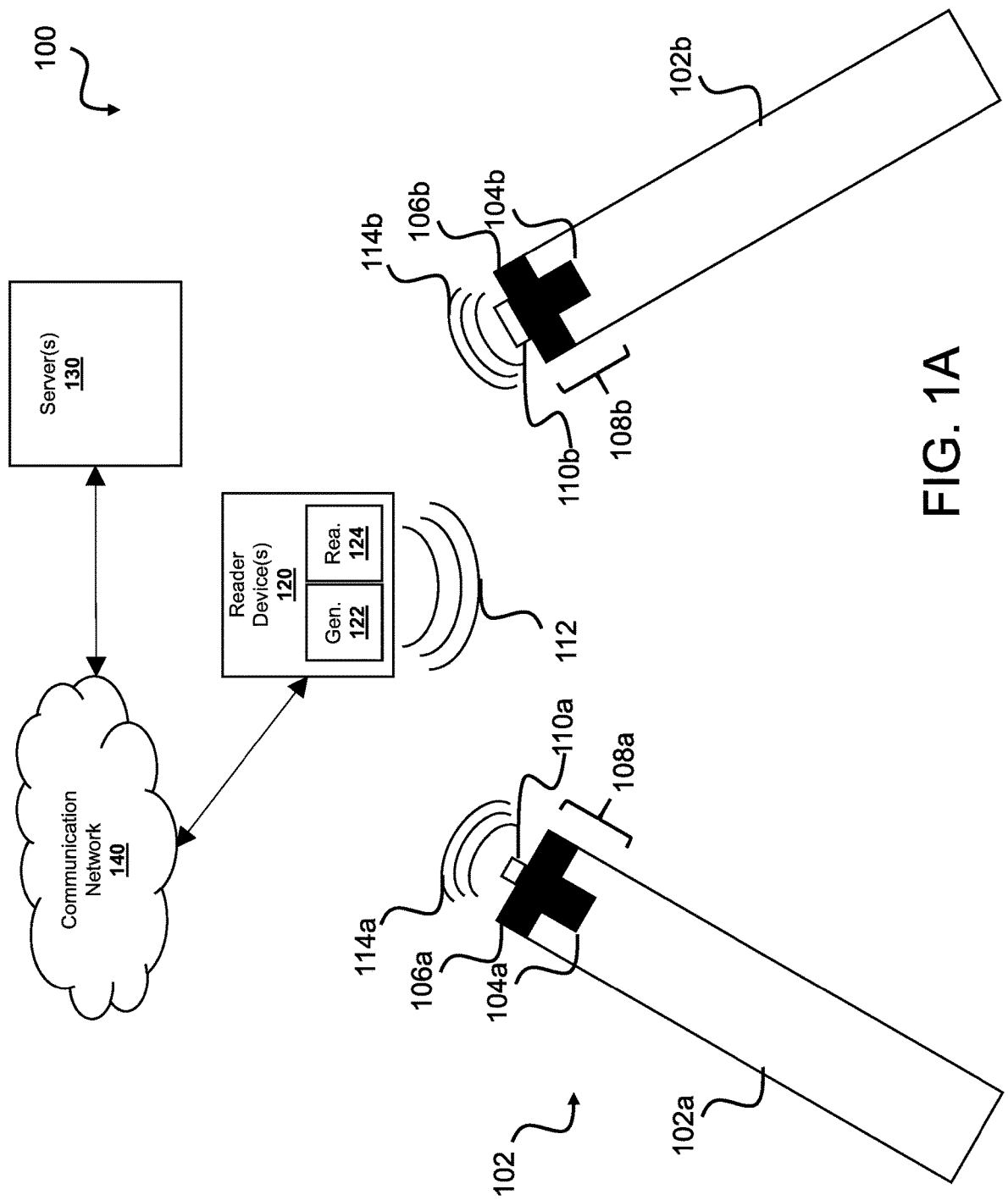
FIG. 1A is a diagram of a non-limiting embodiment or aspect of an environment in which devices, systems, and/or methods, described herein, may be implemented according to the principles of the presently disclosed subject matter.

It is to be understood that the present disclosure may assume various alternative variations and step sequences, except where expressly specified to the contrary. It is also to be understood that the specific devices and processes illustrated in the attached drawings, and described in the following specification, are simply exemplary and non-limiting embodiments or aspects. Hence, specific dimensions and other physical characteristics related to the embodiments or aspects disclosed herein are not to be considered as limiting.

For purposes of the description hereinafter, the terms "end," "upper," "lower," "right," "left," "vertical," "horizontal," "top," "bottom," "lateral," "longitudinal," and derivatives thereof shall relate to the disclosed subject matter as it is oriented in the drawing figures. However, it is to be understood that the disclosed subject matter may assume various alternative variations and step sequences, except where expressly specified to the contrary. It is also to be understood that the specific devices and processes illustrated in the attached drawings, and described in the following specification, are simply exemplary embodiments or aspects of the disclosed subject matter. Hence, specific dimensions and other physical characteristics related to the embodiments or aspects disclosed herein are not to be considered as limiting unless otherwise indicated.

No aspect, component, element, structure, act, step, function, instruction, and/or the like used herein should be construed as critical or essential unless explicitly described as such. Also, as used herein, the articles "a" and "an" are intended to include one or more items and may be used interchangeably with "one or more" and "at least one." Furthermore, as used herein, the term "set" is intended to include one or more items (e.g., related items, unrelated items, a combination of related and unrelated items, and/or the like) and may be used interchangeably with "one or more" or "at least one." Where only one item is intended, the term "one" or similar language is used. Also, as used herein, the terms "has," "have," "having," and/or the like are intended to be open-ended terms. Further, the phrase "based on" is intended to mean "based at least partially on" unless explicitly stated otherwise.

As used herein, the terms "communication" and "communicate" may refer to the reception, receipt, transmission, transfer, provision, and/or the like of information (e.g., data, signals, messages, instructions, commands, and/or the like). For one unit (e.g., a device, a system, a component of a device or system, combinations thereof, and/or the like) to be in communication with another unit means that the one unit is able to directly or indirectly receive information from and/or transmit information to the other unit. This may refer to a direct or indirect connection (e.g., a direct communication connection, an indirect communication connection, and/or the like) that is wired and/or wireless in nature. Additionally, two units may be in communication with each other even though the information transmitted may be modified, processed, relayed, and/or routed between the first and second unit. For example, a first unit may be in communication with a second unit even though the first unit passively receives information and does not actively transmit information to the second unit. As another example, a first unit may be in communication with a second unit if at least one intermediary unit (e.g., a third unit located between the first unit and the second unit) processes information received from the first unit and communicates the processed information to the second unit. In some non-limiting embodiments or aspects, a message may refer to a network packet (e.g., a data packet and/or the like) that includes data. It will be appreciated that numerous other arrangements are possible.

As used herein, the term "server" may refer to one or more computing devices, such as processors, storage devices, and/or similar computer components that communicate with client devices and/or other computing devices over a network, such as the Internet or private networks, and, in some examples, facilitate communication among other servers and/or client devices. It will be appreciated that various other arrangements are possible. In addition, reference to "a server" or "a processor," as used herein, may refer to a previously-recited server and/or processor that is recited as performing a previous step or function, a different server and/or processor, and/or a combination of servers and/or processors. For example, as used in the specification and the claims, a first server and/or a first processor that is recited as performing a first step or function may refer to the same or different server and/or a processor recited as performing a second step or function.

Some non-limiting embodiments or aspects are described herein in connection with thresholds. As used herein, satisfying a threshold may refer to a value being greater than the threshold, more than the threshold, higher than the threshold, greater than or equal to the threshold, less than the threshold, fewer than the threshold, lower than the threshold, less than or equal to the threshold, equal to the threshold, etc.

Non-limiting embodiments or aspects of the disclosed subject matter are directed to devices, systems, and methods for detecting medical device components, including, but not limited to, detection of mating of medical device components. For example, non-limiting embodiments or aspects of the disclosed subject matter provide a first medical device component having at least one first resonant structure (with a first resonant frequency spectrum) and a second medical device component having at least one second resonant structure (with a second resonant frequency spectrum), and upon mating of the first and second medical device components, the first and second resonant structures combine to have a third resonant frequency spectrum (different than the first and second resonant frequency spectra). Such embodiments or aspects provide techniques and systems that enable wirelessly (e.g., via radio communication and/or the like) detecting (e.g., identifying and/or the like) the individual medical device components and/or the mated combination thereof, which may advantageously not require line of sight for operation. For example, since line of sign may not be required, such medical devices may be handled in any way (e.g., any orientation with respect to the reader and/or the like) by a clinician and still be detected. Additionally or alternatively, such embodiments or aspects provide techniques and systems that allow for such wireless detection (e.g., identification and/or the like) without complex circuitry (e.g., integrated circuit, application specific integrated circuit (ASIC), memory, processor, and/or the like) formed on and/or affixed to the medical device components, which may reduce (e.g., decrease and/or the like) the time, the amount of resources, the number of different resources, the expense, and/or the like associated with production and/or use of the disclosed subject matter (e.g., compared to radio frequency identification (RFID) tags and/or the like), may improve reliability (e.g., since there is no complex circuitry to be damaged, degrade, and/or the like), and/or the like. Additionally or alternatively, such embodiments or aspects provide techniques and systems that allow for such wireless detection (e.g., identification and/or the like) without a power source formed on and/or affixed to the medical device components, which may reduce the cost and/or complexity for production and/or use. Additionally or alternatively, such embodiments or aspects provide techniques and systems that are more suitable for automation (e.g., due to wireless operation, reduced (e.g., eliminated, decreased, and/or the like) necessity for line of sight and/or alignment for operation, reduced time and/or expense for production and/or use, and/or the like). Additionally or alternatively, such embodiments or aspects provide techniques and systems that enable detection of mating (e.g., proper connection, alignment, and/or the like) of two or more medical device components. As such, the techniques and systems may be useful for compliance tracking, for example, by tracking (e.g., detecting, logging, and/or the like) connections and/or disconnections of medical device components (e.g., a syringe and a vascular access device). For example, the connections and/or disconnections may be compared with rules (e.g., guidelines, prescribed treatment protocols, and/or the like) to determine compliance therewith. Additionally or alternatively, such embodiments or aspects provide techniques and systems that enable locating and/or tracking of each medical device component within a facility (e.g., using multiple readers located in different (e.g., known) locations of the facility, wherein each reader may detect the medical device component(s) nearby (e.g., within the operating range of the reader and/or the like)). Additionally or alternatively, such embodiments or aspects provide techniques and systems that enable inventory management and/or logistics (e.g., since the number of each type of medical device component and/or location thereof within a facility may be determined at a given time, stock of at least one type of medical device component may be replenished and/or redistributed as needed (e.g., based on satisfying thresholds associated with the stock thereof and/or the like)). Additionally or alternatively, such embodiments or aspects provide techniques and systems that enable anti-counterfeiting (e.g., counterfeit medical device components may lack and/or have the incorrect resonant structure(s) and/or resonant frequency spectrum/spectra).

For the purpose of illustration, in the following description, while the presently disclosed subject matter is described with respect to devices, systems, and methods for detecting medical device components, e.g., detection of mating of medical device components, one skilled in the art will recognize that the disclosed subject matter is not limited to the illustrative embodiments or aspects. For example, the devices, systems, and methods described herein may be used with a wide variety of settings, such as identifying products and/or detecting mating (e.g., of products and/or of components of products) in any setting suitable for using such products, e.g., manufacturing, shipping, inventory management, retail, food products, and/or the like.

Figure 1B:
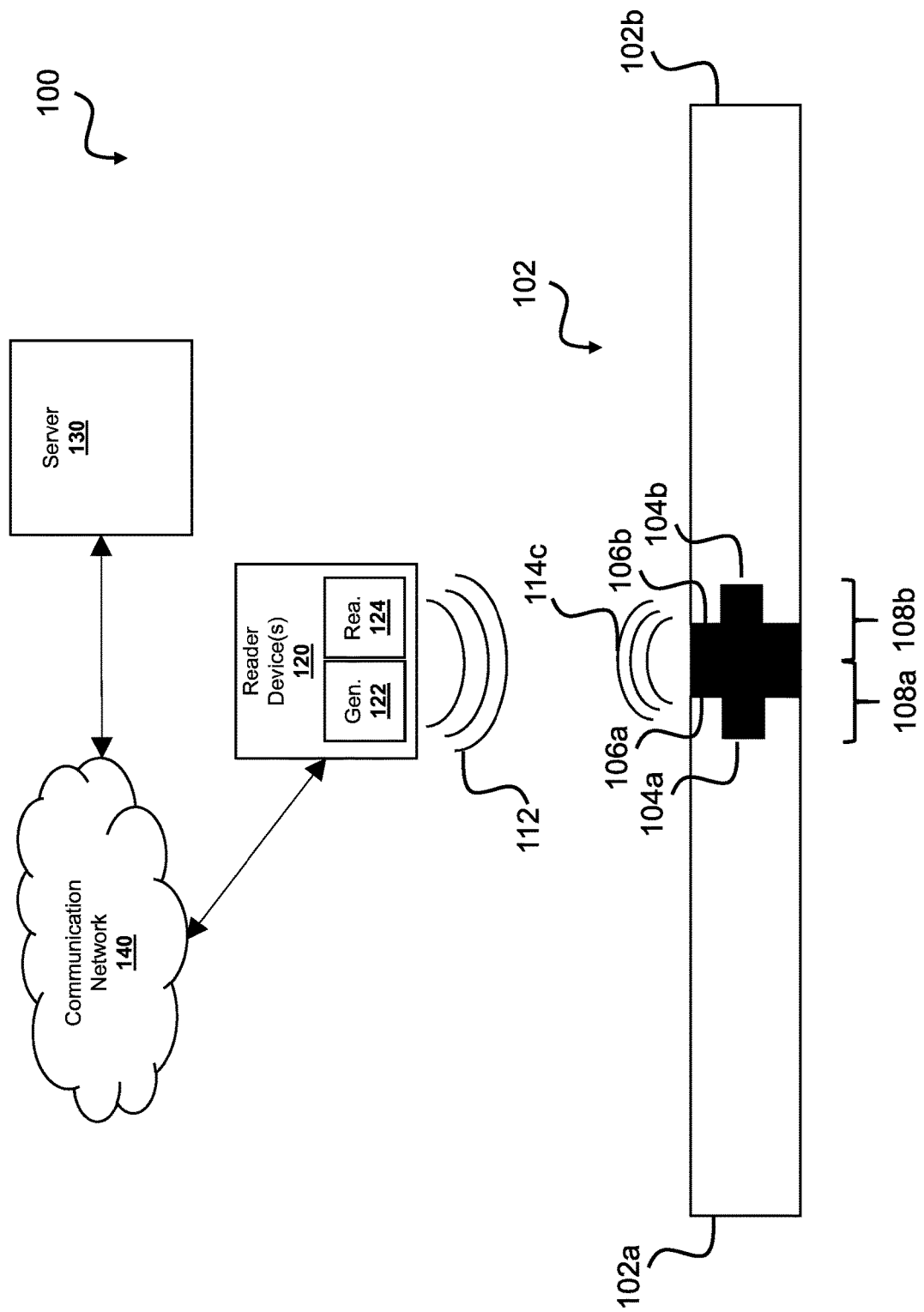
FIG. 1B is a diagram of a non-limiting embodiment or aspect of an environment in which devices, systems, and/or methods, described herein, may be implemented according to the principles of the presently disclosed subject matter.

Referring now to FIGS. 1A and 1B, FIGS. 1A and 1B are diagrams of non-limiting embodiments or aspects of an environment 100 in which devices, systems, and/or methods, as described herein, may be implemented. As shown in FIGS. 1A-1B, environment 100 may include medical device assembly 102, first medical device component 102a, first resonant structure 104a, first metallic strip 106a, first antenna element 108a, first mating element 110a, second medical device component 102b, second resonant structure 104b, second metallic strip 106b, second antenna element 108b, second mating element 110b, interrogation signal 112, first reflected signal 114a, second reflected signal 114b, reader device 120, generator 122, reader 124, server 130, and/or communication network 140.

Medical device assembly 102 may include at least one of first medical device component 102a, second medical device component 102b, any combination thereof, and/or the like.

First medical device component 102a may include at least one device and/or a component thereof configured to be used for medical purposes. For example, first medical device component 102a may include at least one device (e.g., instrument, apparatus, implement, machine, contrivance, implant, any combination thereof, and/or the like) and/or a component thereof, which may be configured for use in the diagnosis of disease or other conditions and/or in the cure, mitigation, treatment, and/or prevention of disease and/or other conditions (e.g., in a human, other animals, and/or the like). In some non-limiting embodiments or aspects, first medical device component 102a may include a syringe.

In some non-limiting embodiments or aspects, first medical device component 102a may include first antenna element 108a. Additionally or alternatively, first antenna element 108a may have a resonant frequency spectrum. For example, first antenna element 108a may include at least one first resonant structure 104a, and each first resonant structure 104a may have a resonant frequency spectrum (e.g., a first resonant frequency spectrum). Additionally or alternatively, first antenna element 108a may include first metallic strip 106a. In some non-limiting embodiments or aspects, first resonant structure 104a may include at least one spiral resonator (e.g., a first spiral resonator). Additionally or alternatively, the first resonant frequency spectrum may include a first natural frequency of the first spiral resonator. In some non-limiting embodiments or aspects, the first spiral resonator may include (e.g., be formed of and/or the like) a first spiral-shaped metallic conductor adjacent to first metallic strip 106a (e.g., of first antenna element 108a of first medical device component 102a). Additionally or alternatively, the first spiral-shaped metallic conductor may have a first inductance, a first capacitance, and/or a first resistance. In some non-limiting embodiments or aspects, the first natural frequency may be based on the first inductance, first capacitance, and/or first resistance. Additionally or alternatively, the first natural frequency, first inductance, first capacitance, and/or first resistance may be based on the geometric properties and/or material properties of the first spiral resonator (e.g., as further described below with respect to FIGS. 2A and 2B). In some non-limiting embodiments or aspects, first resonant structure 104a may include at least one first metal ribbon (e.g., amorphous metal ribbon). Additionally or alternatively, the first resonant frequency spectrum may include a first natural frequency (e.g., resonant frequency and/or the like) of the first metal ribbon (e.g., amorphous metal ribbon). For example, the first natural frequency f (e.g., resonant frequency and/or the like) of the first metal ribbon (e.g., amorphous metal ribbon) may be determined based on the equation $f \approx (1/2\pi)\sqrt{(Y/\rho)}$, where l may represent length, Y may represent Young's modulus, and p may represent density.

In some non-limiting embodiments or aspects, upon interrogation of first medical device component 102a with interrogation signal 112, first antenna element 108a (e.g., first resonant structure 104a thereof) may attenuate at least one first frequency component to form a first attenuated electromagnetic signal (e.g., first reflected signal 114a). For example, interrogation signal 112 may include a multi-frequency electromagnetic signal, and upon interrogation of first medical device component 102a with the multi-frequency electromagnetic signal, first antenna element 108a (e.g., first resonant structure 104a thereof) may attenuate at least one first frequency component of the multi-frequency electromagnetic signal corresponding to the first resonant frequency spectrum to form the first attenuated electromagnetic signal (e.g., as further described below with respect to FIGS. 3A and 3B). In some non-limiting embodiments or aspects, interrogation signal 112 may energize first antenna element 108a (e.g., first resonant structure 104a thereof). Additionally or alternatively, first antenna element 108a (e.g., first resonant structure 104a thereof) may operate independent of (e.g., without and/or the like) a power source. In some non-limiting embodiments or aspects, first antenna element 108a may transmit (e.g., retransmit, backscatter, and/or the like) the first attenuated electromagnetic signal.

In some non-limiting embodiments or aspects, first metallic strip 106a (e.g., at least a portion thereof) may be disposed circumferentially around first medical device component 102a. Additionally or alternatively, first metallic strip 106a (e.g., at least a portion thereof) may be disposed longitudinally (e.g., axially, parallel to the axis of, and/or the like) along first medical device component 102a. In some non-limiting embodiments or aspects, at least a portion of first metallic strip 106a may be disposed at an end (e.g., distal end and/or the like) of the medical device (e.g., so that, upon mating of first medical device component 102a to second medical device component 102b, first metallic strip 106a may electrically contact and/or electromagnetically couple with second metallic strip 106b).

In some non-limiting embodiments or aspects, the at least one first resonant structure 104a may include a plurality of first resonant structures 104a. In some non-limiting embodiments or aspects, the plurality of first resonant structure 104a (and/or a subset thereof) may be disposed circumferentially around first medical device component 102a. Additionally or alternatively, each of the plurality of first resonant structures 104a (and/or a subset thereof) may be disposed longitudinally (e.g., axially, parallel to the axis of, and/or the like) along first medical device component 102a. For example, each first resonant structure 104a (and/or each of a subset thereof) may be disposed at a distinct scale marking on first medical device component 102a (e.g., as further described below with respect to FIG. 6A). In some non-limiting embodiments or aspects, each of the plurality of first resonant structures may include (e.g., be formed of and/or the like) a conductive ink.

In some non-limiting embodiments or aspects, each first resonant structure 104a (and/or a subset thereof) may include (e.g., be formed of and/or the like) temperature-sensitive material(s), humidity-sensitive material(s), light-sensitive material(s), gas-sensitive material(s), any combination thereof, and/or the like. For example, the first natural frequency of such a first resonant structure 104a may change (e.g., increase in frequency, decrease in frequency, and/or the like) based on the temperature, humidity, light, presence of gas, any combination thereof, and/or the like, respectively. Additionally or alternatively, such a first resonant structure 104a may be used for sensing of temperature, humidity, light, presence of gas, any combination thereof, and/or the like in addition to and/or in lieu of identification.

In some non-limiting embodiments or aspects, first medical device component 102a (e.g., first antenna element 108a thereof) may include a first receiving antenna element and a first transmitting antenna element (e.g., as further described below with respect to FIG. 7). For example, each of the first receiving antenna element and the first transmitting antenna element may include a disc-shaped metallic conductor. Additionally or alternatively, the first receiving antenna element and the first transmitting antenna element may be attached at opposite ends of first metallic strip 106a. In some non-limiting embodiments or aspects, the first receiving antenna element and the first transmitting antenna element may be cross-polarized (e.g., to reduce interference between the received signal (e.g., interrogation signal 112) and the reflected signal (e.g., first reflected signal 114a) and/or the like). For example, the first receiving antenna element may be disposed orthogonally to the first transmitting antenna element (e.g., the first receiving antenna element (e.g., a surface thereof) may be disposed in (e.g., substantially in, predominantly in, and/or the like) a first plane and the first transmitting antenna element (e.g., a surface thereof) may be disposed in (e.g., substantially in, predominantly in, and/or the like) a second plane orthogonal to the first plane).

In some non-limiting embodiments or aspects, first medical device component 102a (e.g., first antenna element 108a thereof) may include a first receiving/transmitting antenna element. For example, the first receiving/transmitting antenna element may include a disc-shaped metallic conductor.

In some non-limiting embodiments or aspects, at least a portion of first antenna element 108a (e.g., first resonant structure 104a, first metallic strip 106a, any combination thereof, and/or the like) may be formed on (e.g., printed on and/or the like) first medical device component 102a. Additionally or alternatively, at least a portion of first antenna element 108a (e.g., first resonant structure 104a, first metallic strip 106a, any combination thereof, and/or the like) may be affixed to (e.g., mounted on, adhered to, included with an adhesive tag applied to, and/or the like) first medical device component 102a.

In some non-limiting embodiments or aspects, first medical device component 102a may include first mating element 110a. For example, first mating element 110a may include any element configured to be used for mating first medical device component 102a with second medical device component 102b (e.g., second mating element 110b thereof). In some non-limiting embodiments or aspects, first mating element 110a may include a luer fitting (e.g., a male luer fitting, a female luer fitting, and/or the like). For example, first mating element 110a may include a male luer fitting and second mating element 110b may include a corresponding female luer fitting. In some non-limiting embodiments or aspects, first antenna element 108a (e.g., first resonant structure 104a and/or first metallic strip 106a thereof) may be disposed with first mating element 110a (e.g., male luer fitting and/or the like). For example, at least a portion of first antenna element 108a (e.g., at least a portion of first resonant structure 104a and/or first metallic strip 106a) may surround and/or be disposed proximate to first mating element 110*a*. Additionally or alternatively, at least a portion of first antenna element 108*a* (e.g., at least a portion of first resonant structure 104*a* and/or first metallic strip 106*a*) may be disposed sufficiently close to first mating element 110*a* that, upon mating of first medical device component 102*a* (e.g., first mating element 110*a* thereof) to second medical device component 102*b* (e.g., second mating element 110*b* thereof), first antenna element 108*a* (e.g., first resonant structure 104*a* and/or first metallic strip 106*a*) may electrically contact and/or electromagnetically couple with second antenna element 108*b* (e.g., second resonant structure 104*b* and/or second metallic strip 106*b*).

Second medical device component 102*b* may include at least one device and/or a component thereof configured to be used for medical purposes. For example, second medical device component 102*b* may include at least one device (e.g., instrument, apparatus, implement, machine, contrivance, implant, any combination thereof, and/or the like) and/or a component thereof, which may be configured for use in the diagnosis of disease or other conditions and/or in the cure, mitigation, treatment, and/or prevention of disease and/or other conditions (e.g., in a human, other animals, and/or the like). In some non-limiting embodiments or aspects, second medical device component 102*b* may include a vascular access device (e.g., intravenous (IV) line, catheter, needle, cannula, and/or the like).

In some non-limiting embodiments or aspects, second medical device component 102*b* may include second antenna element 108*b*. Additionally or alternatively, second antenna element 108*b* may have a resonant frequency spectrum. For example, second antenna element 108*b* may include at least one second resonant structure 104*b*, and each second resonant structure 104*b* may have a resonant frequency spectrum (e.g., a second resonant frequency spectrum). Additionally or alternatively, second antenna element 108*b* may include second metallic strip 106*b*. In some non-limiting embodiments or aspects, second resonant structure 104*b* may include at least one spiral resonator (e.g., a second spiral resonator). Additionally or alternatively, the second resonant frequency spectrum may include a second natural frequency of the second spiral resonator. In some non-limiting embodiments or aspects, the second spiral resonator may include (e.g., be formed of and/or the like) a second spiral-shaped metallic conductor adjacent to second metallic strip 106*b* (e.g., of second antenna element 108*b* of second medical device component 102*b*). Additionally or alternatively, the second spiral-shaped metallic conductor may have a second inductance, a second capacitance, and/or a second resistance. In some non-limiting embodiments or aspects, the second natural frequency may be based on the second inductance, second capacitance, and/or second resistance. Additionally or alternatively, the second natural frequency, second inductance, second capacitance, and/or second resistance may be based on the geometric properties and/or material properties of the second spiral resonator (e.g., as further described below with respect to FIGS. 2A and 2B). In some non-limiting embodiments or aspects, the second resonant frequency spectrum may be the same as the first resonant frequency spectrum. In some non-limiting embodiments or aspects, the second resonant frequency spectrum may be different than the first resonant frequency spectrum. Additionally or alternatively, at least one of the first inductance, first capacitance, first resistance, and/or any combination thereof may be different than at least one of the second inductance, second capacitance, second resistance, and/or any combination thereof, respectively. In some non-limiting embodiments or aspects, second resonant structure 104*b* may include at least one second metal ribbon (e.g., amorphous metal ribbon). Additionally or alternatively, the second resonant frequency spectrum may include a second natural frequency (e.g., resonant frequency and/or the like) of the second metal ribbon (e.g., amorphous metal ribbon). For example, the second natural frequency f (e.g., resonant frequency and/or the like) of the second metal ribbon (e.g., amorphous metal ribbon) may be determined based on the equation $f \approx (1/2\pi)\sqrt{(Y/\rho)}$, where l may represent length, Y may represent Young's modulus, and p may represent density.

In some non-limiting embodiments or aspects, upon interrogation of second medical device component 102*b* with interrogation signal 112, second antenna element 108*b* (e.g., second resonant structure 104*b* thereof) may attenuate at least one second frequency component to form a second attenuated electromagnetic signal (e.g., second reflected signal 114*b*). For example, interrogation signal 112 may include a multi-frequency electromagnetic signal, and upon interrogation of second medical device component 102*b* with the multi-frequency electromagnetic signal, second antenna element 108*b* (e.g., second resonant structure 104*b* thereof) may attenuate at least one second frequency component of the multi-frequency electromagnetic signal corresponding to the second resonant frequency spectrum to form the second attenuated electromagnetic signal (e.g., as further described below with respect to FIGS. 3A and 3C). In some non-limiting embodiments or aspects, interrogation signal 112 may energize second antenna element 108*b* (e.g., second resonant structure 104*b* thereof). Additionally or alternatively, second antenna element 108*b* (e.g., second resonant structure 104*b* thereof) may operate independent of (e.g., without and/or the like) a power source. In some non-limiting embodiments or aspects, second antenna element 108*b* may transmit (e.g., retransmit, backscatter, and/or the like) the second attenuated electromagnetic signal.

In some non-limiting embodiments or aspects, second metallic strip 106*b* (e.g., at least a portion thereof) may be disposed circumferentially around second medical device component 102*a*. Additionally or alternatively, second metallic strip 106*b* (e.g., at least a portion thereof) may be disposed longitudinally (e.g., axially, parallel to the axis of, and/or the like) along second medical device component 102*b*. In some non-limiting embodiments or aspects, at least a portion of second metallic strip 106*b* may be disposed at an end (e.g., distal end and/or the like) of the medical device (e.g., so that, upon mating of first medical device component 102*a* to second medical device component 102*b*, first metallic strip 106*a* may electrically contact and/or electromagnetically couple with second metallic strip 106*b*).

In some non-limiting embodiments or aspects, the at least one second resonant structure 104*b* may include a plurality of second resonant structures 104*b*. In some non-limiting embodiments or aspects, the plurality of second resonant structures 104*b* (and/or a subset thereof) may be disposed circumferentially around second medical device component 102*b*. Additionally or alternatively, each of the plurality of second resonant structures 104*b* (and/or a subset thereof) may be disposed longitudinally (e.g., axially, parallel to the axis of, and/or the like) along second medical device component 102*b*. For example, each second resonant structure 104*b* (and/or each of a subset thereof) may be disposed at a distinct scale marking on second medical device component 102*b* (e.g., as further described below with respect to FIG. 6A). In some non-limiting embodiments or aspects, each of the plurality of second resonant structures 104b may include (e.g., be formed of and/or the like) a conductive ink.

In some non-limiting embodiments or aspects, each second resonant structure 104b (and/or a subset thereof) may include (e.g., be formed of and/or the like) temperature-sensitive material(s), humidity-sensitive material(s), light-sensitive material(s), gas-sensitive material(s), any combination thereof, and/or the like. For example, the second natural frequency of such a second resonant structure 104b may change (e.g., increase in frequency, decrease in frequency, and/or the like) based on the temperature, humidity, light, presence of gas, any combination thereof, and/or the like, respectively. Additionally or alternatively, such a second resonant structure 104b may be used for sensing of temperature, humidity, light, presence of gas, any combination thereof, and/or the like in addition to and/or in lieu of identification.

In some non-limiting embodiments or aspects, second medical device component 102b (e.g., second antenna element 108b thereof) may include a second receiving antenna element and a second transmitting antenna element (e.g., as further described below with respect to FIG. 7). For example, each of the second receiving antenna element and the second transmitting antenna element may include a disc-shaped metallic conductor. Additionally or alternatively, the second receiving antenna element and the second transmitting antenna element may be attached at opposite ends of second metallic strip 106b. In some non-limiting embodiments or aspects, the second receiving antenna element and the second transmitting antenna element may be cross-polarized (e.g., to reduce interference between the received signal (e.g., interrogation signal 112) and the reflected signal (e.g., second reflected signal 114b) and/or the like). For example, the second receiving antenna element may be disposed orthogonally to the second transmitting antenna element (e.g., the second receiving antenna element (e.g., a surface thereof) may be disposed in (e.g., substantially in, predominantly in, and/or the like) a second plane and the second transmitting antenna element (e.g., a surface thereof) may be disposed in (e.g., substantially in, predominantly in, and/or the like) a second plane orthogonal to the second plane).

In some non-limiting embodiments or aspects, second medical device component 102b (e.g., second antenna element 108b thereof) may include a second receiving/transmitting antenna element. For example, the second receiving/transmitting antenna element may include a disc-shaped metallic conductor.

In some non-limiting embodiments or aspects, at least a portion of second antenna element 108b (e.g., second resonant structure 104b, second metallic strip 106b, any combination thereof, and/or the like) may be formed on (e.g., printed on and/or the like) second medical device component 102b. Additionally or alternatively, at least a portion of second antenna element 108b (e.g., second resonant structure 104b, second metallic strip 106b, any combination thereof, and/or the like) may be affixed to (e.g., mounted on, adhered to, included with an adhesive tag applied to, and/or the like) second medical device component 102b.

In some non-limiting embodiments or aspects, second medical device component 102b may include second mating element 110b. For example, second mating element 110b may include any element configured to be used for mating second medical device component 102b with first medical device component 102a (e.g., first mating element 110a thereof). In some non-limiting embodiments or aspects, second mating element 110b may include a luer fitting (e.g., a male luer fitting, a female luer fitting, and/or the like). For example, second mating element 110b may include a female luer fitting and first mating element 110a may include a corresponding male luer fitting. In some non-limiting embodiments or aspects, second antenna element 108b (e.g., second resonant structure 104b and/or second metallic strip 106b thereof) may be disposed with second mating element 110b (e.g., female luer fitting and/or the like). For example, at least a portion of second antenna element 108b (e.g., at least a portion of second resonant structure 104b and/or second metallic strip 106b) may surround and/or be disposed proximate to second mating element 110b. Additionally or alternatively, at least a portion of second antenna element 108b (e.g., at least a portion of second resonant structure 104b and/or second metallic strip 106b) may be disposed sufficiently close to second mating element 110b that, upon mating of second medical device component 102b (e.g., second mating element 110b thereof) to first medical device component 102a (e.g., first mating element 110a thereof), second antenna element 108b (e.g., second resonant structure 104b and/or second metallic strip 106b) may electrically contact and/or electromagnetically couple with first antenna element 108a (e.g., first resonant structure 104a and/or first metallic strip 106a).

In some non-limiting embodiments or aspects, upon mating of first medical device component 102a (e.g., first mating element 110a thereof) to second medical device component 102b (e.g., second mating element 110b thereof), first antenna element 108a (e.g., first resonant structure 104a thereof) and second antenna element 108b (e.g., second resonant structure 104b thereof) may combine to have a third resonant frequency spectrum (e.g., as shown in FIG. 1B). Additionally or alternatively, the third resonant frequency spectrum may be different than the first resonant frequency spectrum and the second resonant frequency spectrum. In some non-limiting embodiments or aspects, upon mating of first medical device component 102a (e.g., first mating element 110a thereof) to second medical device component 102b (e.g., second mating element 110b thereof), the antenna elements thereof (e.g., first antenna element 108a (e.g., first resonant structure 104a and/or first metallic strip 106a thereof) and second antenna element 108b (e.g., second resonant structure 104b and/or first metallic strip 106b thereof)) may act as a combined antenna element (e.g., due to electrical contact, electromagnetic coupling, and/or the like, as described herein). For example, upon mating of first medical device component 102a (e.g., first mating element 110a thereof) to second medical device component 102b (e.g., second mating element 110b thereof), first resonant structure 104a (e.g., the first spiral resonator) and second resonant structure 104b (e.g., the second spiral resonator) may be coupled (e.g., electromagnetically coupled and/or the like) to form a resonant circuit having a third natural frequency. Additionally or alternatively, the third resonant frequency spectrum may include the third natural frequency of the resonant circuit.

In some non-limiting embodiments or aspects, upon interrogation of the mated medical device components (e.g., first medical device component 102a and second medical device component 102b upon mating) with interrogation signal 112, the antenna elements thereof (e.g., first antenna element 108a (e.g., first resonant structure 104a thereof) and second antenna element 108b (e.g., second resonant structure 104b thereof)) may attenuate at least one third frequency component to form a third attenuated electromagnetic signal (e.g., third reflected signal 114c). For example, interrogation signal 112 may include a multi-frequency electromagnetic signal, and upon interrogation of the mated medical device components with the multi-frequency electromagnetic signal, the antenna elements thereof (e.g., first resonant structure 104a and second resonant structure 104b thereof) may attenuate at least one third frequency component of the multi-frequency electromagnetic signal corresponding to the third resonant frequency spectrum to form the third attenuated electromagnetic signal (e.g., as further described below with respect to FIGS. 3A and 3D). In some non-limiting embodiments or aspects, interrogation signal 112 may energize antenna elements (e.g., first antenna element 108a, second antenna element 108b, and/or the like). Additionally or alternatively, the antenna elements may operate independent of (e.g., without and/or the like) a power source. In some non-limiting embodiments or aspects, at least one of the antenna elements (e.g., first antenna element 108a, second antenna element 108b, and/or the like) may transmit (e.g., retransmit, backscatter, and/or the like) the third attenuated electromagnetic signal.

Reader device 120 may include one or more devices capable of receiving information from and/or communicating information to server 130 and/or the like (e.g., via network 140). Additionally or alternatively, each reader device 120 may include a device capable of receiving information from and/or communicating information to other reader devices 120 (e.g., via network 140, another network (e.g., an ad hoc network, a local network, a private network, a virtual private network, and/or the like), and/or any other suitable communication technique). In some non-limiting embodiments or aspects, reader device 120 may or may not be capable of receiving information (e.g., from another reader device 120) via a short-range wireless communication connection (e.g., a near-field communication (NFC) communication connection, an RFID communication connection, a Bluetooth® communication connection, a Zigbee® communication connection, and/or the like), and/or communicating information (e.g., to another reader device 120) via a short-range wireless communication connection.

In some non-limiting embodiments or aspects, each reader device 120 may include at least one of generator 122, reader 124, and/or any combination thereof. Additionally or alternatively, at least one of generator 122, reader 124, and/or any combination thereof may be separate from reader device 120, and reader device 120 may include a device capable of receiving information from and/or communicating information to generator 122 and/or reader 124 (e.g., via network 140, another network (e.g., an ad hoc network, a local network, a private network, a virtual private network, and/or the like), and/or any other suitable communication technique).

Generator 122 may include at least one transmitter (e.g., at least one device and/or circuit configured to generate and/or transmit electromagnetic waves, such as a signal generator, a radio frequency (RF) transmitter, a microwave transmitter, an analog transmitter, a digital transmitter, any combination thereof, and/or the like). Additionally or alternatively, generator 122 may generate alternating current (e.g., RF alternating current, microwave alternating current, and/or the like). In some non-limiting embodiments or aspects, reader device 120 and/or generator 122 may include at least one antenna (e.g., antenna element, dipole antenna, and/or the like). Additionally or alternatively, generator 122 may apply the alternating current to the antenna, which may be excited by the alternating current to thereby transmit electromagnetic waves (e.g., radio waves, microwaves, and/or the like). In some non-limiting embodiments or aspects, generator 122 may include one or more devices capable of receiving information from and/or communicating information to reader device 120, server 130, and/or the like (e.g., via network 140).

In some non-limiting embodiments or aspects, generator 122 may transmit interrogation signal 112 (e.g., to the medical device assembly 102). For example, interrogation signal 112 may include a multi-frequency electromagnetic signal, as described herein. In some non-limiting embodiments or aspects, interrogation signal 112 may include a continuous wave, multi-frequency electromagnetic signal of uniform amplitude and phase.

Reader 124 may include at least one receiver (e.g., at least one device and/or circuit configured to receive electromagnetic waves). In some non-limiting embodiments or aspects, reader device 120 and/or reader 124 may include at least one antenna (e.g., antenna element, dipole antenna, and/or the like). Additionally or alternatively, the antenna may receive (e.g., intercept and/or the like) electromagnetic waves to thereby generate alternating currents. Additionally or alternatively, such alternating currents may be applied (e.g., by the antenna) to the receiver, which may extract information therefrom. For example, the receiver may determine which frequency components are present in the received signal (e.g., received electromagnetic waves and/or the like).

In some non-limiting embodiments or aspects, reader 124 may receive at least one reflected signal (e.g., first reflected signal 114a, second reflected signal 114b, third reflected signal 114c, any combination thereof, and/or the like) from the medical device assembly 102. For example, upon interrogation of medical device assembly 102 with interrogation signal 112 (e.g., a multi-frequency electromagnetic signal), reader 124 may receive (e.g., from medical device assembly 102) at least one reflected signal (e.g., first reflected signal 114a, second reflected signal 114b, third reflected signal 114c, any combination thereof, and/or the like), which may include an attenuated electromagnetic signal (e.g., first, second, and/or third attenuated electromagnetic signal associated with first medical device component 102a, second medical device component 102a, and/or mated medical device components, respectively), as described herein. In some non-limiting embodiments or aspects, each reflected signals (e.g., first reflected signal 114a, second reflected signal 114b, third reflected signal 114c, any combination thereof, and/or the like) may include a backscattered signal, a retransmitted signal, any combination thereof, and/or the like.

In some non-limiting embodiments or aspects, reader 124 may detect a respective resonant frequency spectrum (e.g., first, second, and/or third resonant frequency spectrum associated with first medical device component 102a, second medical device component 102a, and/or mated medical device components, respectively) by at least one of an amplitude attenuation, a phase jump, a frequency attenuation, any combination thereof, and/or the like in the reflected signal(s). For example, upon interrogation of first medical device component 102a with interrogation signal 112, reader 124 may detect first resonant frequency spectrum by at least one of an amplitude attenuation, a phase jump, a frequency attenuation, any combination thereof, and/or the like in the at least one reflected signal corresponding to the first resonant frequency spectrum. Additionally or alternatively, upon interrogation of second medical device component 102b with interrogation signal 112, reader 124 may detect the second resonant frequency spectrum by at least one of an amplitude attenuation, a phase jump, a frequency attenuation, any combination thereof, and/or the like in the at least one reflected signal corresponding to the second resonant frequency spectrum. Additionally or alternatively, upon interrogation of the mated medical device components (e.g., first medical device component 102a mated with second medical device component 102b) with interrogation signal 112, reader 124 may detect the third resonant frequency spectrum by at least one of an amplitude attenuation, a phase jump, a frequency attenuation, any combination thereof, and/or the like in the at least one reflected signal corresponding to the third resonant frequency spectrum.

In some non-limiting embodiments or aspects, reader 124 and/or reader device 120 may communicate reflected signal data associated with the reflected signal (e.g., to server 130 via network 140 and/or the like). For example, reader 124 and/or reader device 120 may include a communication interface for such communication.

In some non-limiting embodiments or aspects, the at least one reader 124 may include a plurality of readers. Additionally or alternatively, each reader 124 may be disposed at a location (e.g., known location, predetermined location, selectable location, preselected location, any combination thereof, and/or the like) within at least one site (e.g., at least one facility, at least one building, and/or the like). For example, the location of each reader 124 may be different than the location of all other readers 124 (e.g., each reader 124 may be at a different location within the site(s)). In some non-limiting embodiments or aspects, a location of medical device assembly 102 may be determined (e.g., by reader 124, reader device 120, server 130, and/or the like) based on which reader 124 of the plurality of readers 124 detects medical device assembly 102 (e.g., the respective reader 124 may have a known location, and the location of medical device assembly 102 may be determined to be proximate to (e.g., within operating range of) the respective reader 124 that detected medical device assembly 102).

In some non-limiting embodiments or aspects, generator 122 and/or reader 124 may be included in a single device (e.g., reader device 120 and/or the like). Additionally or alternatively, generator 122 and/or reader 124 may share a single antenna (e.g., antenna of reader device 120 and/or the like). In some non-limiting embodiments or aspects, generator 122 and/or reader 124 may be separate devices.

Server 130 may include one or more devices capable of receiving information from and/or communicating information to reader device 120, generator 122, reader 124, and/or the like (e.g., via network 140). For example, server 130 may include one or more computing devices such as a server, a group of servers, and/or the like. In some non-limiting embodiments or aspects, server 130 may be associated with a facility, as described herein. In some non-limiting embodiments or aspects, server 130 may be in communication with a data storage device, which may be local or remote to server 130. In some non-limiting embodiments or aspects, server 130 may be capable of receiving information from, storing information in, communicating information to, or searching information stored in the data storage device.

In some non-limiting embodiments or aspects, server 130 may include a second communication interface configured to communicate with the first communication interface (e.g., of reader 124, reader device 120, and/or the like via network 140 and/or the like). Additionally or alternatively, server 130 may be configured to receive the reflected signal data over the first network. In some non-limiting embodiments or aspects, the first server is configured to store the reflected signal data (e.g., in a database, a data storage device, a memory, any combination thereof, and/or the like).

In some non-limiting embodiments or aspects, each type of medical device component (e.g., first medical device component 102a, second medical device component 102b, and/or the like, as described herein) may have a unique identifier (e.g., stock keeping unit (SKU) and/or the like). Additionally or alternatively, each unique identifier may be associated with a respective resonant frequency spectrum (e.g., first resonant frequency spectrum, second resonant frequency spectrum, and/or the like, as described herein). In some non-limiting embodiments or aspects, each mated combination of medical device components (e.g., first medical device component 102a mated with second medical device component 102b and/or the like, as described herein) may have a respective resonant frequency spectrum (e.g., third resonant frequency spectrum and/or the like, as described herein). In some non-limiting embodiments or aspects, each type of medical device component and/or each mated combination of medical device components may be uniquely identified based on the respective resonant frequency spectrum thereof. For example, server 130 may store a mapping (e.g., database, table, and/or the like) of each type of medical device component (e.g., unique identifier thereof) and/or each mated combination of medical device components to the respective resonant frequency spectrum thereof (which may be predetermined, preselected, and/or the like).

In some non-limiting embodiments or aspects, a unique respective resonant frequency spectrum may be assigned to each individual type of medical device component (e.g., first medical device component 102a, second medical device component 102b, and/or the like, as described herein) and/or to each mated combination of medical device components based on at least one rule. For example, a first rule may include that no two different types of medical device components may be assigned to the same resonant frequency spectrum (e.g., $\forall 1 \leq i, j \leq N$, if $i \neq j$ then $F_i \neq F_j$, where N may represent the total number of possible types of medical device components, i may represent a number associated with a first type of medical device component, $F_i$ may represent the resonant frequency spectrum of the first type of medical device component, j may represent a number associated with a second type of medical device component, and $F_j$ may represent the resonant frequency spectrum of the second type of medical device component). Additionally or alternatively, a second rule may include that no two types of medical device components (e.g., whether the same or different type of medical device component) when mated (e.g., physically connected, electrically connected, electromagnetically coupled, and/or the like) may have a respective resonant frequency spectrum of any other two types of medical device components when mated (e.g., $\forall 1 \leq i, j, k, l \leq N$, if $i \neq k$ and/or $j \neq l$ then $\phi(S_i, S_j) \neq \phi(S_k, S_l)$, where i may represent a number associated with a first type of medical device component, j may represent a number associated with a second type of medical device component, k may represent a number associated with a third type of medical device component, l may represent a number associated with a fourth type of medical device component, $S_i$ may represent the properties (e.g., geometric properties, material properties, and/or the like) of at least one resonant structure associated with the first type of medical device component, $S_j$ may represent the properties (e.g., geometric properties, material properties, and/or the like) of at least one resonant structure associated with the second type of medical device component, $S_k$ may represent the properties (e.g., geometric properties, material properties, and/or the like) of at least one resonant structure associated with the third type of medical device component, $S_l$ may represent the properties (e.g., geometric properties, material properties, and/or the like) associated of at least one resonant structure with the fourth type of medical device component, and ϕ may represent the resonant frequency spectrum of two the resonant structure(s) associated with the mated combination of two types of medical device components). Additionally or alternatively, a third rule may include that no one type of medical device component may have a respective resonant frequency spectrum of a mated combination of any two types of medical device components (e.g., $\forall 1 \leq i, j, k \leq N\ F_i \neq \phi(S_j, S_k)$), wherein where i may represent a number associated with a first type of medical device component, j may represent a number associated with a second type of medical device component, k may represent a number associated with a third type of medical device component, $F_i$ may represent the resonant frequency spectrum of the first type of medical device component, $S_j$ may represent the properties (e.g., geometric properties, material properties, and/or the like) of at least one resonant structure associated with the second type of medical device component, $S_k$ may represent the properties (e.g., geometric properties, material properties, and/or the like) of at least one resonant structure associated with the third type of medical device component, and ϕ may represent the resonant frequency spectrum of two the resonant structure(s) associated with the mated combination of two types of medical device components).

In some non-limiting embodiments or aspects, server 130 may perform and/or assist with inventory management. For example, a threshold (e.g., minimum number and/or the like) may be selected (e.g., predetermined, preselected, dynamically selected, and/or the like) for a total number of each type of medical device component at the site(s). Additionally or alternatively, since each type of medical device component may be uniquely identified based on the respective resonant frequency spectrum thereof, server 130 may determine a number of each type of medical device component within the site(s) (e.g., based on reflected signal data received from a plurality of readers 124 within the site(s)). In some non-limiting embodiments or aspects, if the total number of a respective type of medical device component satisfies the threshold (e.g., is less than the minimum number and/or the like), server 130 may determine that the stock of the respective type of medical device component may need to be replenished. For example, server 130 may communicate a notification (e.g., email, text message, and/or the like) indicating that the stock of the respective type of medical device component may need to be replenished. Additionally or alternatively, server 130 may automatically order additional stock of the respective type of medical device component (e.g., via e-commerce and/or the like). Additionally or alternatively, server 130 may initiate any suitable replenishment approach, such as those implemented within healthcare institutions (e.g., requesting carts to run between stock room, pharmacy, and/or care area site where a medical device may be utilized and/or the like). In some non-limiting embodiments or aspects, at least one local threshold (e.g., minimum number and/or the like) may be selected (e.g., predetermined, preselected, dynamically selected, and/or the like) for a number of each type of medical device component at a respective location within the site. Additionally or alternatively, since each type of medical device component may be uniquely identified based on the respective resonant frequency spectrum thereof, server 130 may determine a number of each type of medical device component at the respective location within the site(s) (e.g., based on reflected signal data received from a plurality of readers 124 within the site(s)). In some non-limiting embodiments or aspects, if the number of a respective type of medical device component at the respective location satisfies the threshold (e.g., is less than the minimum number and/or the like), server 130 may determine that the stock of the respective type of medical device component may need to be replenished and/or redistributed from other locations within the site. For example, server 130 may communicate a notification and/or automatically order additional stock, as described herein.

For the purpose of illustration, if a medical device component (e.g., first medical device component 102a, a syringe, and/or the like) were filled with a drug (e.g., in a pharmacy of a site and/or the like) and then transported to another location (e.g., an operating room of the site and/or the like), the medical device component may be detected during transportation and/or at the destination location by at least one reader 124 (e.g., any of one or more readers 124 that might be disposed along the path that the medical device component may travel and/or any of one or more readers 124 that might be disposed in the destination location). As such, a location of the medical device component may be determined and/or stored, as described herein. For example, a location of the respective reader 124 that most recently detected the medical device component may be known (e.g., preselected, predetermined, and/or the like). Additionally or alternatively, when the medical device component arrives at the destination location, it may be detected by at least one reader 124 disposed in or near the destination location (e.g., the operating room and/or the like). Additionally or alternatively, if the drug-filled medical device component is intended to be connected to a second medical device component (e.g., second medical device component 102b, a catheter, and/or the like), e.g., to deliver the drug to the patient, the mating between the drug-filled medical device component and the second medical device component may be detected, as described herein. Additionally or alternatively, after detecting the resonant frequency spectrum associated with mating of the drug-filled medical device component and the second medical device component, if at least one reader 124 (e.g., in or near the destination location) later (e.g., within a predetermined selected (e.g., predetermined, preselected, dynamically selected, and/or the like) period of time and/or the like) detects a first resonant frequency spectrum associated with the medical device component and a second resonant frequency spectrum associated with the second medical device component (e.g., and no longer detects the resonant frequency spectrum associated with mating between these medical device components), disconnection between such medical device components may be determined (e.g., detected, inferred, assumed, and/or the like).

In some non-limiting embodiments or aspects, server 130 (and/or reader device 120 and/or reader 124) may perform and/or assist with compliance determinations. For example, since mating of first medical device component 102a and second medical device component 102b may be detected based on detecting the third frequency spectrum (and/or the lack of mating between first medical device component 102a and second medical device component 102b may be detected based on detecting at least one of the first frequency spectrum and/or the second frequency spectrum without detecting the third frequency spectrum), connections and/or disconnections of the medical device components may be determined (e.g., detected, monitored, logged, stored, and/or the like). For example, based on the reflected signal data, server 130 (and/or reader device 120 and/or reader 124) may determine whether first medical device component 102a and second medical device component 102b were mated and/or may store the reflected signal data with time data (e.g., time stamp, time and date data, and/or the like). In some non-limiting embodiments or aspects, the determined mating of first medical device component 102a and second medical device component 102b (and/or the lack thereof) may be compared to guidelines and/or prescribed treatment protocols to determine compliance therewith (e.g., if guidelines and/or prescribed treatment protocols call for connection between two components for a period of time (e.g., an amount of time for flushing an IV line by connecting a syringe with saline thereto, an amount of time for a fluid to be infused through an IV line by connecting a container (e.g., bag) of such fluid to the IV line, and/or the like), the time stamps associated with mating between the medical device components or lack thereof may be compared to the period of time of the guidelines and/or prescribed treatment protocols). For example, such guidelines and/or prescribed treatment protocols may be stored in a database (e.g., local or remote to server 130).

In some non-limiting embodiments or aspects, the operating frequencies of first antenna element 108a (e.g., first resonant structure 104a thereof), second antenna element 108b (e.g., second resonant structure 104b thereof), reader device 120, generator 122, reader 124, and/or the like may include any suitable frequency range. For example, the operating frequency may be in the ultra-wide band (UWB), in the range of 3-10 GHz, and/or the like. In some non-limiting embodiments or aspects, the operating range (e.g., distance and/or the like) of first antenna element 108a (e.g., first resonant structure 104a thereof), second antenna element 108b (e.g., second resonant structure 104b thereof), reader device 120, generator 122, reader 124, and/or the like may include any suitable distance. For example, the operating range (e.g., distance and/or the like) may be less than 5 m, less than 1 m, less than 0.7 m, and/or the like. In some non-limiting embodiments or aspects, the operating temperature range of first antenna element 108a (e.g., first resonant structure 104a thereof), second antenna element 108b (e.g., second resonant structure 104b thereof), reader device 120, generator 122, reader 124, and/or the like may include any suitable temperature range. For example, the operating temperature range may include −20° C. to 80° C. and/or the like.

In some non-limiting embodiments or aspects, resonant structures as described herein (e.g., first antenna element 108a including at least one first resonant structure 104a, second antenna element 108b including at least one second resonant structure 104b, and/or the like) may be used in addition to RFID tags (e.g., RFID tags including integrated circuits (ICs), ASICs, and/or the like). For example, the resonant structures as described herein (e.g., first antenna element 108a including at least one first resonant structure 104a, second antenna element 108b including at least one second resonant structure 104b, and/or the like) may be used to detect mating of medical device components while at least one RFID tag may be used to identify each individual medical device component and/or the like.

Network 140 may include one or more wired and/or wireless networks. For example, network 140 may include a cellular network (e.g., a long-term evolution (LTE) network, a third generation (3G) network, a fourth generation (4G) network, a fifth generation (5G) network, a code division multiple access (CDMA) network, and/or the like), a public land mobile network (PLMN), a local area network (LAN), a wide area network (WAN), a metropolitan area network (MAN), a telephone network (e.g., the public switched telephone network (PSTN)), a private network (e.g., a private network associated with a facility), an ad hoc network, an intranet, the Internet, a fiber optic-based network, a computer network, a cloud computing network, and/or the like, and/or a combination of these or other types of networks.

The number and arrangement of systems, devices, and/or networks shown in FIG. 1 are provided as an example. There may be additional systems, devices, and/or networks; fewer systems, devices, and/or networks; different systems, devices, and/or networks; and/or differently arranged systems, devices, and/or networks than those shown in FIG. 1. Furthermore, two or more systems or devices shown in FIG. 1 may be implemented within a single system or device, or a single system or device shown in FIG. 1 may be implemented as multiple, distributed systems or devices. Additionally or alternatively, a set of systems (e.g., one or more systems) or a set of devices (e.g., one or more devices) of environment 100 may perform one or more functions described as being performed by another set of systems or another set of devices of environment 100.

Figure 2A:
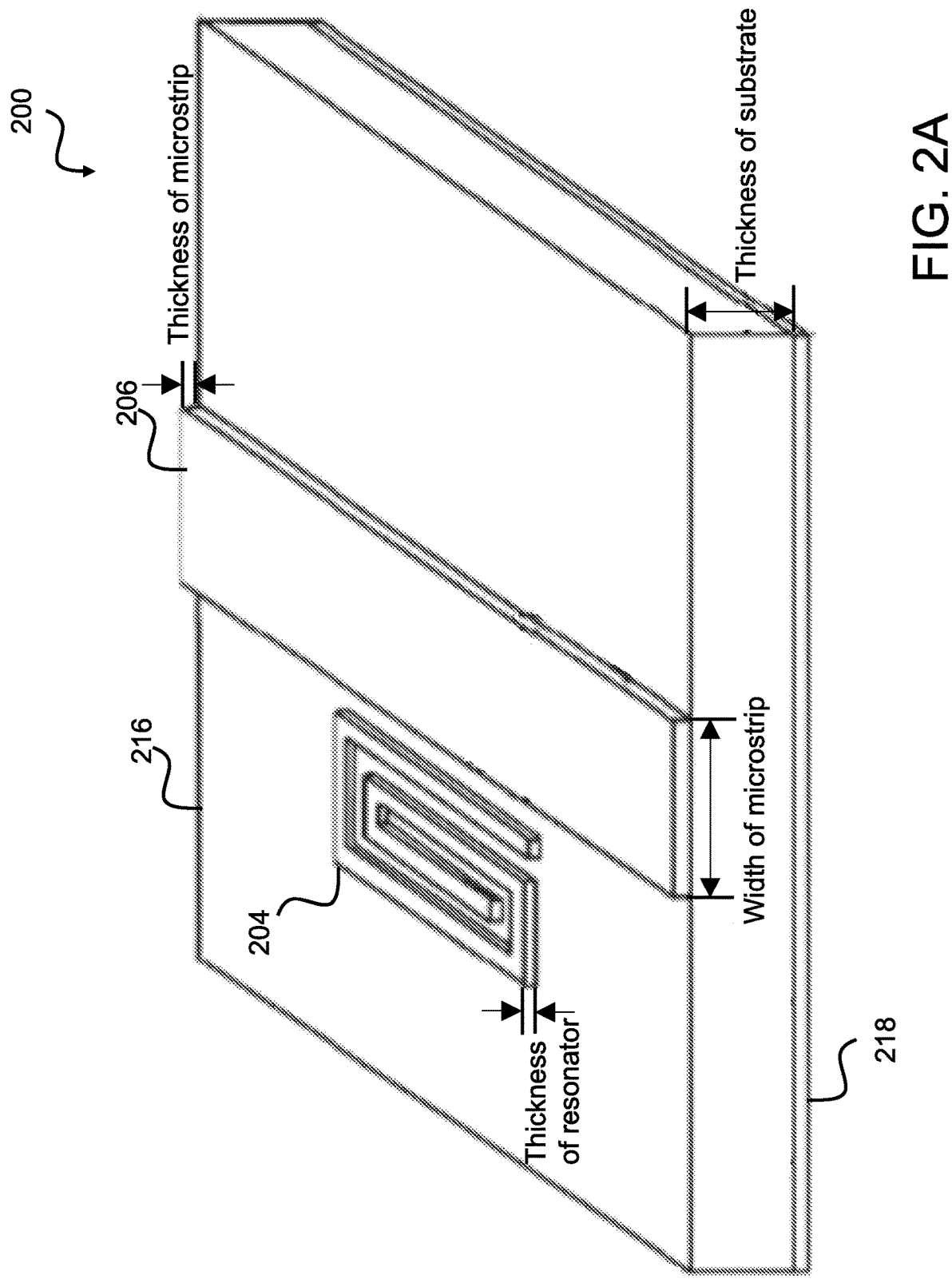
FIG. 2A is a diagram of a non-limiting embodiment or aspect of an implementation of one or more systems and/or one or more devices of FIG. 1 according to the principles of the presently disclosed subject matter.
Figure 2B:
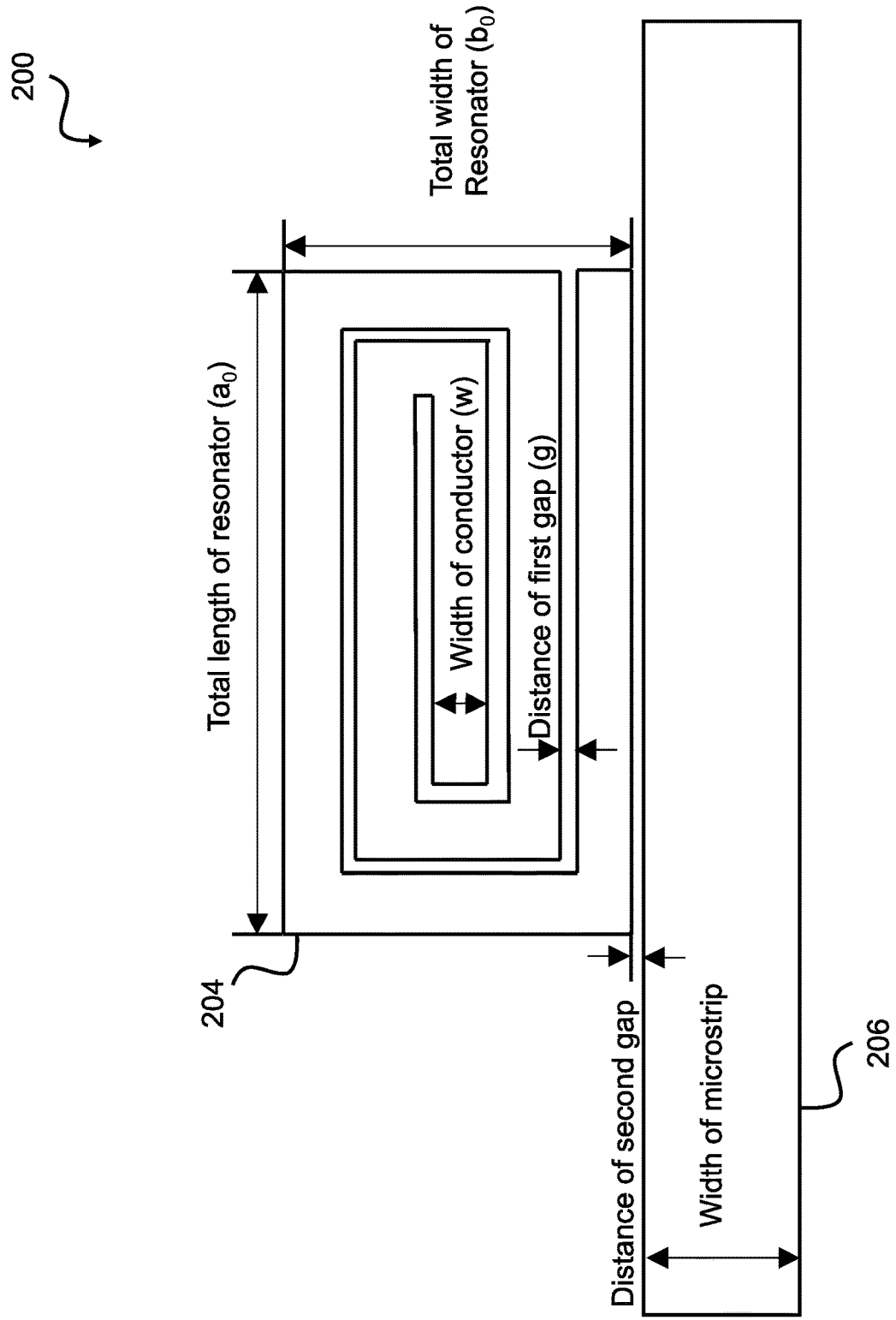
FIG. 2B is a diagram of a non-limiting embodiment or aspect of an implementation of one or more systems and/or one or more devices of FIG. 1 according to the principles of the presently disclosed subject matter.

Referring now to FIGS. 2A-2D, FIGS. 2A-2D are diagrams of an exemplary implementation 200 of a non-limiting embodiment or aspect relating to environment 100 shown in FIG. 1. As shown in FIGS. 2A and 2B, implementation 200 may include spiral resonator 204, microstrip 206, substrate 216, and/or ground plane 218. In some non-limiting embodiments or aspects, spiral resonator 204 may be the same as or similar to first resonant structure 104a and/or second resonant structure 104b. In some non-limiting embodiments or aspects, microstrip 206 may be the same as or similar to first metallic strip 106a and/or second metallic strip 106b.

In some non-limiting embodiments or aspects, spiral resonator 204, microstrip 206, and/or ground plane 218 may include (e.g., be formed of and/or the like) a conductive material (e.g., conductor, metallic material, conductive ink, a metal ribbon (e.g., amorphous metal ribbon), and/or the like). For example, each of spiral resonator 204, microstrip 206, and/or ground plane 218 may include (e.g., be formed of and/or the like) the same conductive material. Additionally or alternatively, at least one of spiral resonator 204, microstrip 206, and/or ground plane 218 may include (e.g., be formed of and/or the like) a different conductive material than the others. In some non-limiting embodiments or aspects, at least one of spiral resonator 204, microstrip 206, and/or ground plane 218 may include (e.g., be formed of and/or the like) aluminum, copper, gold, silver, aluminum oxide, conductive ink, transparent conductive material, and/or the like.

In some non-limiting embodiments or aspects, substrate 216 may include (e.g., be formed of and/or the like) the material of (at least a portion of) the respective medical device component (e.g., first medical device component 102a, second medical device component 102b, and/or the like). Additionally or alternatively, substrate 216 may include (e.g., be formed of and/or the like) a tag (e.g., that will be affixed to the respective medical device component). For example, the tag may include (e.g., be formed of and/or the like) a dielectric material (e.g., plastic, flexible polymer, polypropylene, polyethylene terephthalate (PET), paper, transparent dielectric material, and/or the like).

In some non-limiting embodiments or aspects, spiral resonator 204 may include (e.g., be formed of and/or the like) a spiral-shaped conductive material adjacent to microstrip 206. Additionally or alternatively, spiral resonator 204 may have an inductance (L), first capacitance (C), and/or a resistance (R). In some non-limiting embodiments or aspects, the natural frequency of spiral resonator 204 may be based on the inductance, capacitance, and/or a resistance. Additionally or alternatively, the natural frequency, inductance, capacitance, and/or resistance may be based on the geometric properties and/or material properties of spiral resonator 204, microstrip 206, substrate 216, and/or ground plane 218. In some non-limiting embodiments or aspects, spiral resonator 204 may have geometric properties including a thickness, a total length, a total width, a width of the conductive material (of spiral resonator 204), a distance of a first gap (e.g., separating adjacent turns of conductive material), a number of turns, and/or the like. Additionally or alternatively, spiral resonator 204 (e.g., the conductive material thereof) may have material properties including a resistivity, a conductivity, a density, a Young's modulus, and/or the like. In some non-limiting embodiments or aspects, microstrip 206 may have geometric properties including a thickness, a width, and/or the like. Additionally or alternatively, microstrip 206 (e.g., the conductive material thereof) may have material properties including a resistivity, a conductivity, a density, a Young's modulus, and/or the like. In some non-limiting embodiments or aspects, substrate 216 may have geometric properties including a thickness and/or the like. Additionally or alternatively, substrate 216 may have material properties including a dielectric permittivity and/or the like. In some non-limiting embodiments or aspects, ground plane 218 (e.g., the conductive material thereof) may have material properties including a resistivity, a conductivity, a density, a Young's modulus, and/or the like. In some non-limiting embodiments or aspects, the natural frequency, inductance, capacitance, and/or resistance of spiral resonator 204 may be tuned (e.g., selected, modified, and/or the like) based on tuning (e.g., selecting, modifying, and/or the like) the geometric properties and/or material properties of spiral resonator 204, microstrip 206, substrate 216, and/or ground plane 218.

In some non-limiting embodiments or aspects, the natural frequency, inductance, capacitance, and/or resistance of spiral resonator 204 may be determined based on the geometric properties and/or material properties of spiral resonator 204, microstrip 206, substrate 216, and/or ground plane 218, as described in R. Fletcher, *Low-Cost Electromagnetic Tagging: Design and Implementation*, Massachusetts Institute of Technology (2002), the disclosure of which is incorporated by reference herein in its entirety.

In some non-limiting embodiments or aspects, the natural frequency of a spiral resonator (e.g., spiral resonator 204) may be based on resonance (e.g., frequency-dependent stimulated response characterized by an amplitude response at the natural frequency (and/or a narrow frequency band around the natural frequency)). For example, such an amplitude response may indicate that the spiral resonator (e.g., spiral resonator 204) may be able to store energy at the natural frequency (e.g., resonant frequency and/or the like). In some non-limiting embodiments or aspects, a ratio of total stored energy to the dissipated energy per unit cycle may be referred to as the quality factor Q, which may be determined based on the following equation:

$$Q = \frac{W_{max}}{P/\omega_0} = \frac{\omega_0 W_{max}}{P} = \frac{\omega_0(w_E + w_M)}{P} = \frac{\omega_0\left(\frac{1}{2}w_E^{max} + \frac{1}{2}w_M^{max}\right)}{P}$$

where $W_{max}$ may represent the maximum stored energy, P may represent the time-averaged power dissipated by the spiral resonator (e.g., spiral resonator 204), $\omega_0$ may represent the natural frequency (e.g., resonant frequency and/or the like), $w_E$ may represent the electric stored energy, $w_M$ may represent the magnetic stored energy, $w_E^{max}$ may represent the maximum electric stored energy, and $w_M^{max}$ may represent the maximum magnetic stored energy.

In some non-limiting embodiments or aspects, the resistance of a spiral resonator (e.g., spiral resonator 204) may be based on the resistivity (e.g., bulk resistivity and/or the like) of the material of the spiral resonator, the cross-sectional area of the material (e.g. width of the material multiplied by thickness of the material and/or the like) of the spiral resonator, and the length of the material of the spiral resonator, and/or the like. For example, the resistance R may be determined based on the following equation:

$$R = \frac{\rho l}{A}$$

where $\rho$ may represent the bulk resistivity, l may represent the length of the material of the spiral resonator, and A may represent the cross-sectional area of the material of the spiral resonator.

In some non-limiting embodiments or aspects, the inductance of a spiral resonator (e.g., spiral resonator 204) may be based on the length of the spiral resonator, the width of the spiral resonator, the thickness of the spiral resonator, the number of turns of the spiral resonator, the magnetic permeability of the material of the spiral resonator, the cross-section of the material of the spiral resonator, and/or the like. For example, the inductance L may be determined (e.g., estimated and/or the like) based on the following equations:

$$d = \frac{2 \cdot (t + w)}{\pi}$$

$$a_{avg} = a_0 - N \cdot (g+w)$$

$$b_{avg} = b_0 - N \cdot (g+w)$$

$$x_1 = a_{avg} \cdot \ln\left[\frac{2 \cdot a_{avg} \cdot b_{avg}}{d \cdot \left(a_{avg} + \sqrt{a_{avg}^2 \cdot b_{avg}^2}\right)}\right]$$

$$x_2 = b_{avg} \cdot \ln\left[\frac{2 \cdot a_{avg} \cdot b_{avg}}{d \cdot \left(b_{avg} + \sqrt{a_{avg}^2 \cdot b_{avg}^2}\right)}\right]$$

$$x_3 = 2\left[a_{avg} + b_{avg} - \sqrt{a_{avg}^2 \cdot b_{avg}^2}\right]$$

$$x_4 = \frac{a_{avg} + b_{avg}}{4}$$

$$L \approx \frac{\mu_0}{\pi} \cdot (x_1 + x_2 - x_3 + x_4) \cdot N^p$$

where t may represent the thickness of the spiral resonator, w may represent the width of the conductor of the spiral resonator, $a_0$ may represent the total length of the spiral resonator, $a_{avg}$ may represent the average length of a turn of the spiral resonator, $b_0$ may represent the total width of the spiral resonator, $b_{avg}$ may represent the average width of a turn of the spiral resonator, N may represent the number of turns of the spiral resonator, g may represent the distance of the gap between turns of the spiral resonator (e.g., the first gap), $\mu_0$ may represent the magnetic permeability, and p may represent a constant based on the geometric cross-section of the material of the spiral resonator (e.g., p may be approximately equal to 1.8).

In some non-limiting embodiments or aspects, the capacitance of a spiral resonator (e.g., spiral resonator 204) may be based on the length of the spiral resonator, the width of the spiral resonator, the thickness of the substrate (e.g., substrate 216), the number of turns of the spiral resonator, the dielectric permittivity of the substrate, and/or the like. For example, the capacitance C may be determined (e.g., estimated and/or the like) based on the following equation:

$$C = \frac{\varepsilon}{t_\varepsilon}[2 \cdot a_{avg} + 2 \cdot b_{avg}] \cdot N$$

where ε may represent the dielectric permittivity of the substrate, $t_\varepsilon$ may represent the thickness of the spiral resonator, $a_{avg}$ may represent the average length of a turn of the spiral resonator, $b_{avg}$ may represent the average width of a turn of the spiral resonator, and N may represent the number of turns of the spiral resonator.

In some non-limiting embodiments or aspects, the natural frequency (e.g., resonant frequency and/or the like) of a spiral resonator (e.g., spiral resonator 204) may be based on the inductance and the capacitance of the spiral resonator. For example, the natural frequency (e.g., resonant frequency and/or the like) $\omega_0$ may be determined based on the following equation:

$$\omega_0 = \frac{1}{\sqrt{LC}}$$

where L may represent the inductance and C may represent the capacitance.

Figure 2D:
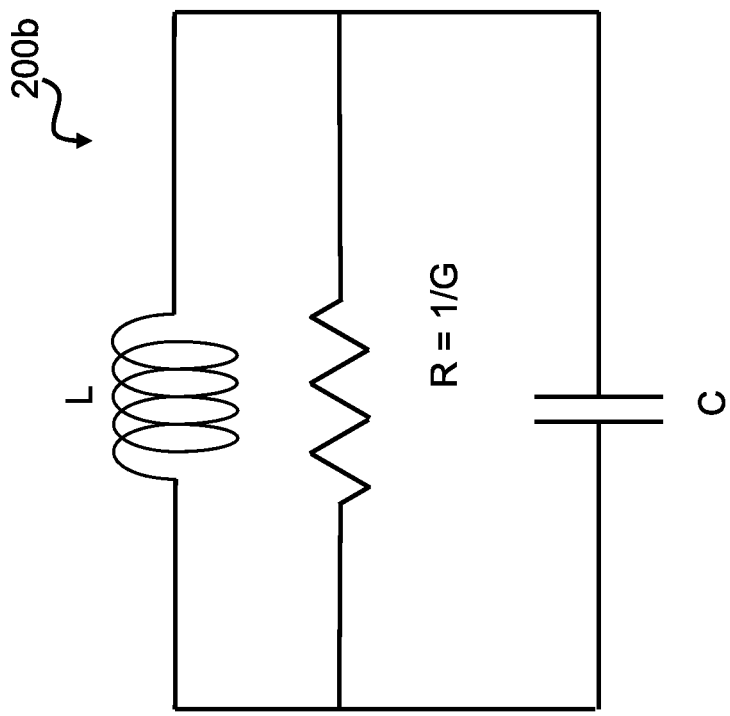
FIG. 2D is a diagram of a non-limiting embodiment or aspect of an implementation of one or more systems and/or one or more devices of FIG. 1 according to the principles of the presently disclosed subject matter.
Figure 2C:
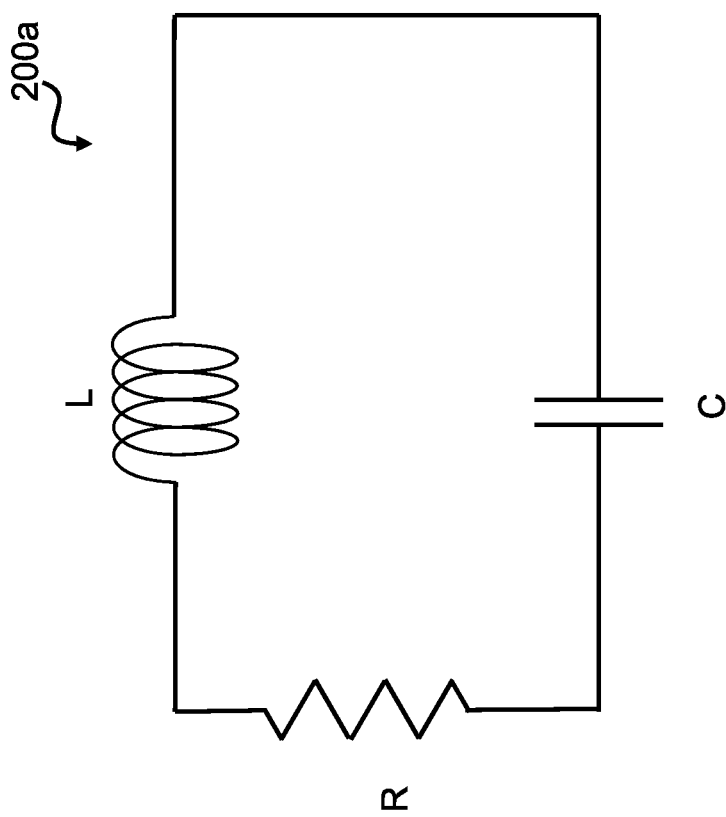
FIG. 2C is a diagram of a non-limiting embodiment or aspect of an implementation of one or more systems and/or one or more devices of FIG. 1 according to the principles of the presently disclosed subject matter.
Figure 4A:
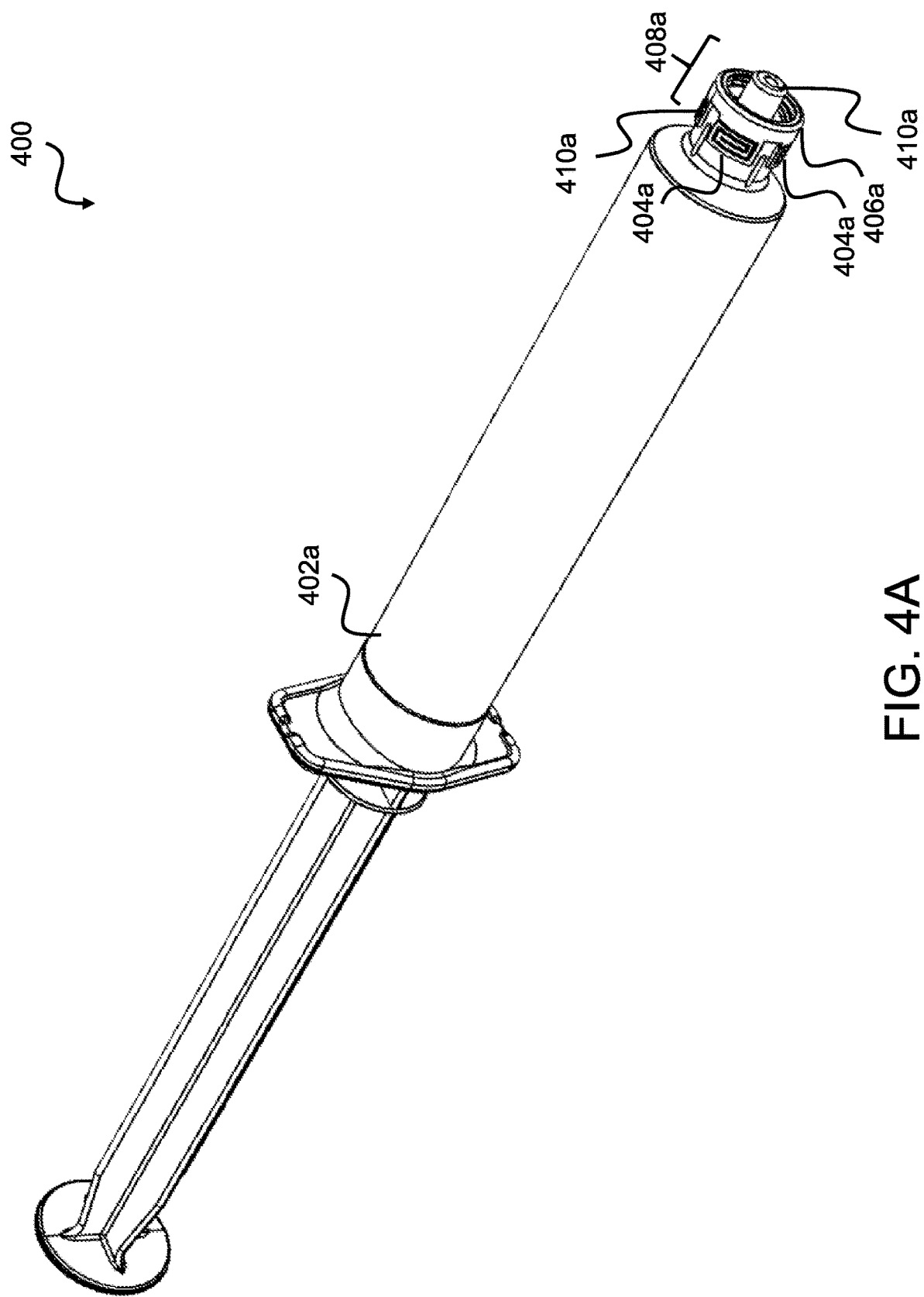
FIG. 4A is a diagram of a non-limiting embodiments or aspects of an implementation of one or more systems and/or one or more devices of FIG. 1 according to the principles of the presently disclosed subject matter.
Figure 4B:
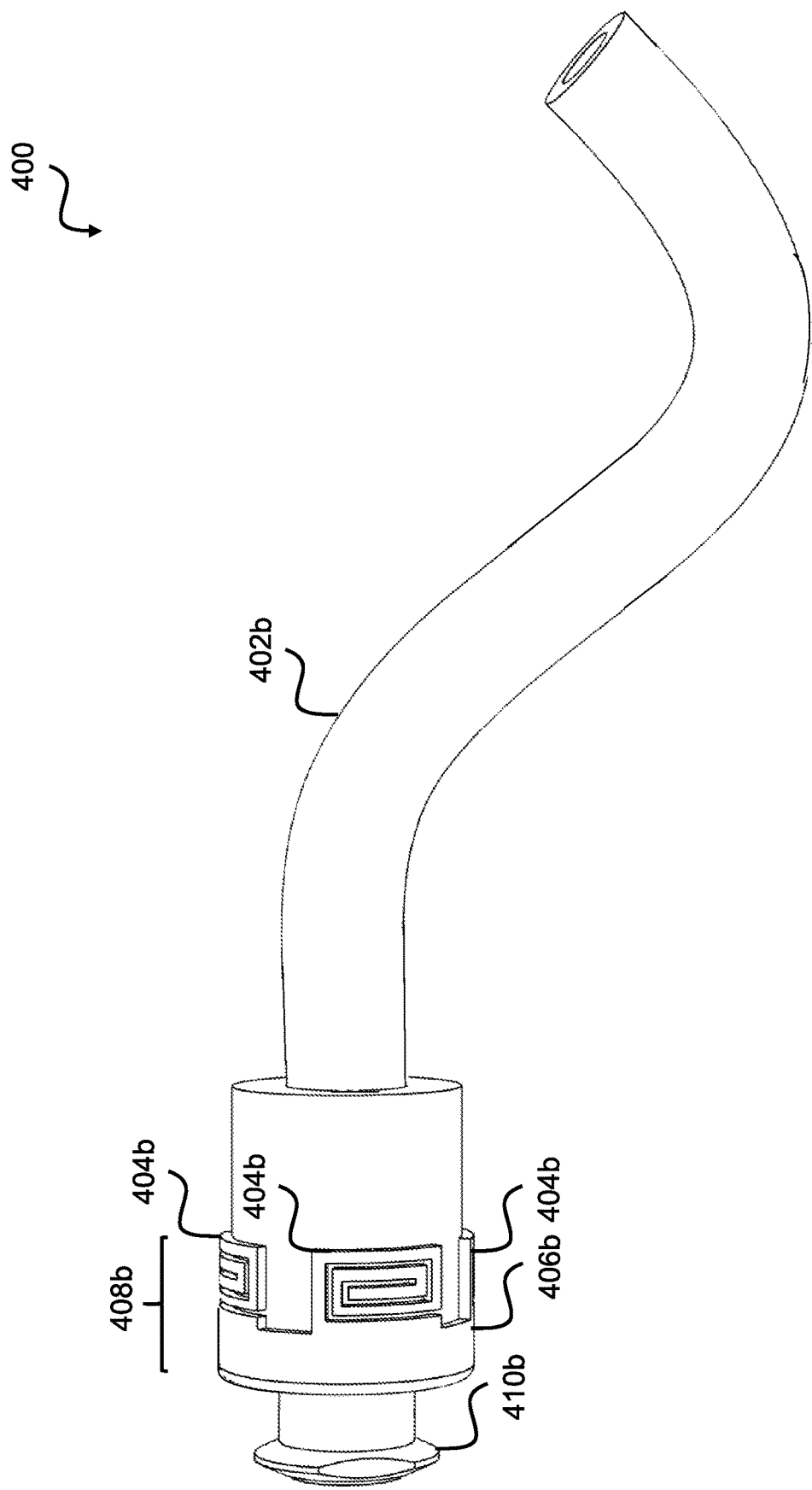
FIG. 4B is a diagram of a non-limiting embodiments or aspects of an implementation of one or more systems and/or one or more devices of FIG. 1 according to the principles of the presently disclosed subject matter.
Figure 4C:
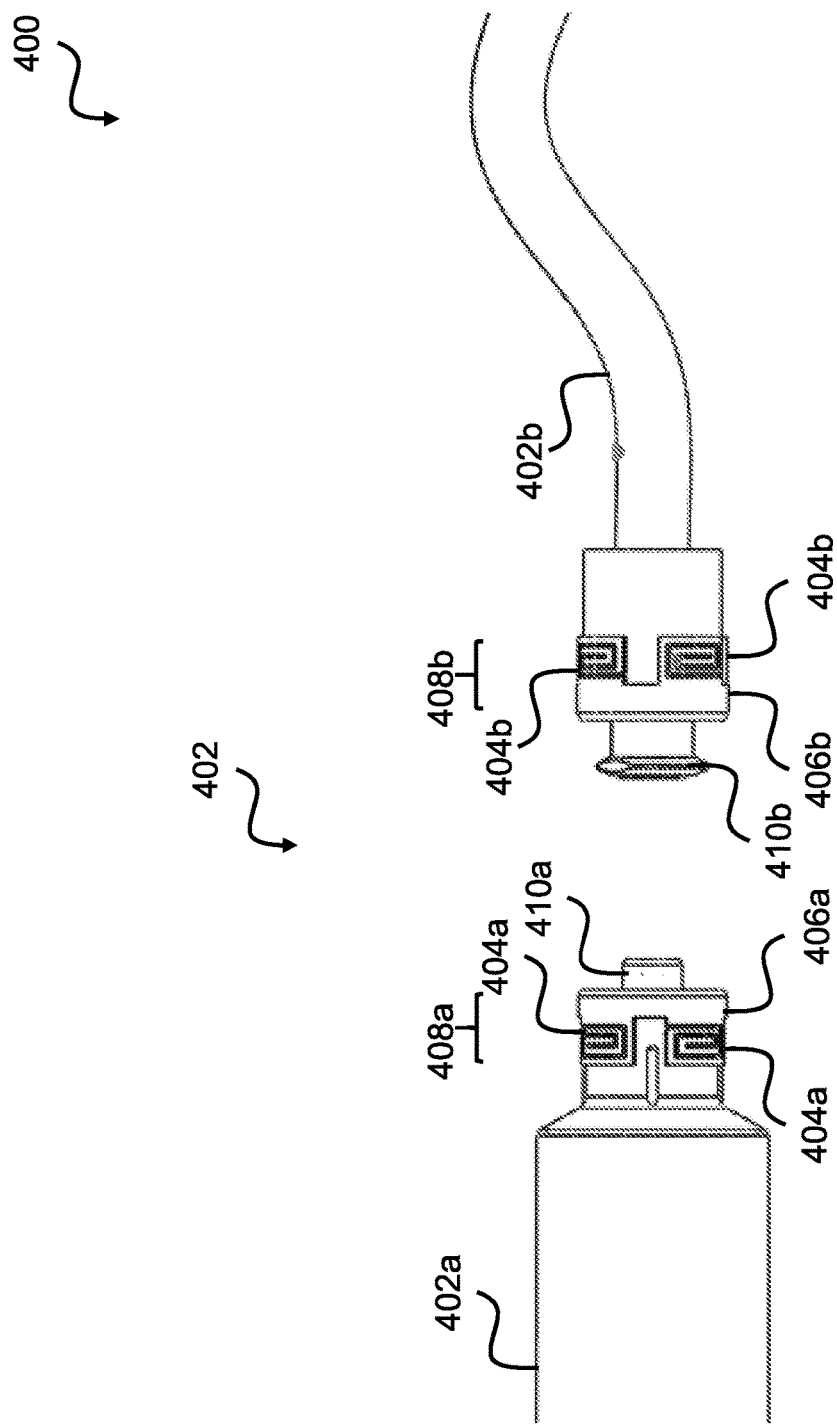
FIG. 4C is a diagram of a non-limiting embodiments or aspects of an implementation of one or more systems and/or one or more devices of FIG. 1 according to the principles of the presently disclosed subject matter.
Figure 4D:
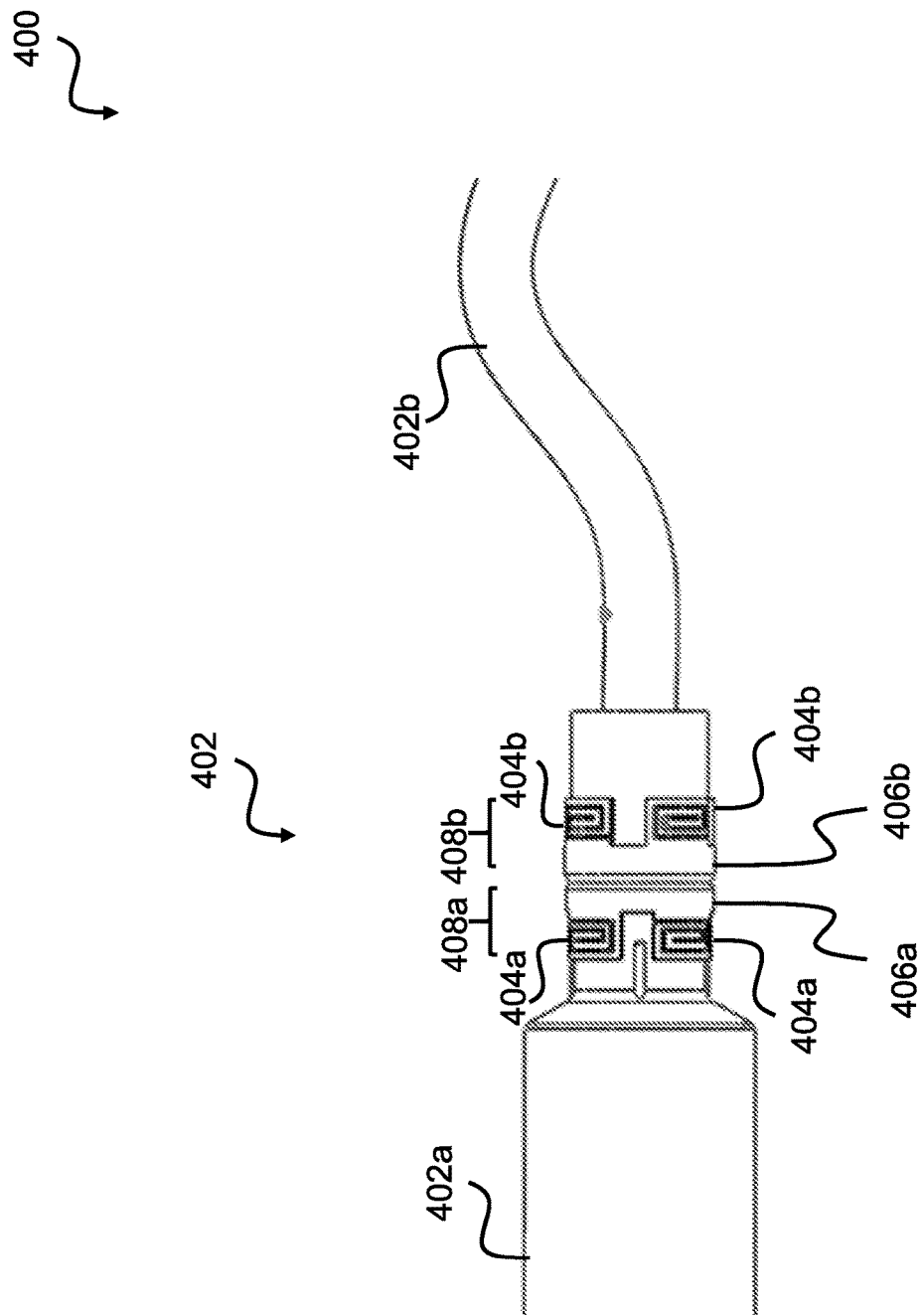
FIG. 4D is a diagram of a non-limiting embodiments or aspects of an implementation of one or more systems and/or one or more devices of FIG. 1 according to the principles of the presently disclosed subject matter.

Referring to FIG. 2C, circuit 200a may include an equivalent circuit associated with implementation 200 having series resonance. As shown in FIG. 2C, circuit 200a may include inductance L, capacitance C, and/or resistance R. In some non-limiting embodiments or aspects, resistance R may be modeled as being in series with inductance L and capacitance C. In some non-limiting embodiments or aspects, inductance L, capacitance C, and/or resistance R may be determined as described herein. For example, at least one of inductance L, capacitance C, and/or resistance R may be determined (e.g., estimated and/or the like) based on the equations above.

In some non-limiting embodiments or aspects, the operating frequency (e.g., natural frequency and/or the like) of spiral resonator 204 and/or the like may include any suitable frequency range. For example, the operating frequency may be in the ultra-wide band (UWB), in the range of 3-10 GHz, and/or the like. In some non-limiting embodiments or aspects, the operating range (e.g., distance and/or the like) of spiral resonator 204 and/or the like may include any suitable distance. For example, the operating range (e.g., distance and/or the like) may be less than 5 m, less than 1 m, less than 0.7 m, and/or the like. In some non-limiting embodiments or aspects, the operating temperature range of spiral resonator 204 and/or the like may include any suitable temperature range. For example, the operating temperature range may include −20° C. to 80° C. and/or the like. In some non-limiting embodiments or aspects, the weight of resonator 204 and/or the like may be less than 5 g. In some non-limiting embodiments or aspects, the width ($b_0$) and length ($a_0$) of resonator 204 and/or the like may include any suitable width and length. For example, the width and length may be in the ranges of 10 mm width by 10 mm length to 16 cm width by 16 cm length, 25 mm width by 70 mm length to 88 mm width by 65 mm length, 2 cm width by 4 cm length to 16 cm width by 16 cm length, and/or the like. In some non-limiting embodiments or aspects, the cost of each spiral resonator 204 may be less than 1 cent.

Referring to FIG. 2D, circuit 200b may include an equivalent circuit associated with implementation 200 having parallel resonance. As shown in FIG. 2D, circuit 200b may include inductance L, capacitance C, and/or resistance R. In some non-limiting embodiments or aspects, resistance R may be modeled as being in parallel with inductance L and capacitance C. In some non-limiting embodiments or aspects, inductance L, capacitance C, and/or resistance R may be determined as described herein. For example, at least one of inductance L, capacitance C, and/or resistance R may be determined (e.g., estimated and/or the like) based on the equations above.

Referring now to FIGS. 3A-3D, FIGS. 3A-3D are graphs of exemplary frequency spectra of an implementation of a non-limiting embodiment or aspect relating to environment 100 shown in FIG. 1. As shown in FIGS. 3A-3D, a graph may have a horizontal axis associated with frequency (f) and a vertical axis associated with amplitude (A).

Referring to FIG. 3A, interrogation signal 312 may include a multi-frequency electromagnetic signal, as described herein. For example, interrogation signal 312 may include a continuous wave, multi-frequency electromagnetic signal of uniform amplitude and phase across a range of frequencies. In some non-limiting embodiments or aspects, interrogation signal 312 may be the same as or similar to interrogation signal 112.

Referring to in FIG. 3B, first reflected signal 314a may include a first attenuated electromagnetic signal, as described herein. For example, first reflected signal 314a may include at least one of an amplitude attenuation, a phase jump, a frequency attenuation, any combination thereof, and/or the like corresponding to a first resonant frequency spectrum (e.g., associated with first medical device component 102a and/or first resonant structure 104a thereof), as described herein. For the purpose of illustration, as shown in FIG. 3B, first reflected signal 314a may include an amplitude attenuation around first natural frequency $f_1$ (e.g., associated with first resonant structure 104a and/or the like).

In some non-limiting embodiments or aspects, first reflected signal 314a may be the same as or similar to first reflected signal 114a.

Referring to in FIG. 3C, second reflected signal 314b may include a second attenuated electromagnetic signal, as described herein. For example, second reflected signal 314b may include at least one of an amplitude attenuation, a phase jump, a frequency attenuation, any combination thereof, and/or the like corresponding to a second resonant frequency spectrum (e.g., associated with second medical device component 102b and/or second resonant structure 104b thereof), as described herein. For the purpose of illustration, as shown in FIG. 3C, second reflected signal 314b may include an amplitude attenuation around second natural frequency $f_2$ (e.g., associated with second resonant structure 104b and/or the like). In some non-limiting embodiments or aspects, second reflected signal 314b may be the same as or similar to second reflected signal 114b.

Referring to in FIG. 3D, third reflected signal 314c may include a third attenuated electromagnetic signal, as described herein. For example, third reflected signal 314c may include at least one of an amplitude attenuation, a phase jump, a frequency attenuation, any combination thereof, and/or the like corresponding to a third resonant frequency spectrum (e.g., associated with the mated combination of first medical device component 102a and second medical device component 102b and/or the like), as described herein. For the purpose of illustration, as shown in FIG. 3D, third reflected signal 314c may include an amplitude attenuation around third natural frequency $f_3$ (e.g., associated with the electromagnetically coupled combination of first resonant structure 104a and second resonant structure 104b and/or the like). In some non-limiting embodiments or aspects, third reflected signal 314c may be the same as or similar to third reflected signal 114c.

Referring now to FIGS. 4A-4D, FIGS. 4A-4D are diagrams of an exemplary implementation 400 of a non-limiting embodiment or aspect relating to environment 100 shown in FIG. 1. As shown in FIGS. 4A-4D, implementation 400 may include medical device assembly 402, first medical device component 402a, first resonant structure 404a, first metallic strip 406a, first antenna element 408a, first mating element 410a, second medical device component 402b, second resonant structure 404b, second metallic strip 406b, second antenna element 408b, and/or second mating element 410b. In some non-limiting embodiments or aspects, medical device assembly 402 may be the same as or similar to medical device assembly 102. In some non-limiting embodiments or aspects, first medical device component 402a may be the same as or similar to first medical device component 102a. In some non-limiting embodiments or aspects, first resonant structure 404a may be the same as or similar to first resonant structure 104a. In some non-limiting embodiments or aspects, first metallic strip 406a may be the same as or similar to first metallic strip 106a. In some non-limiting embodiments or aspects, first antenna element 408a may be the same as or similar to first antenna element 108a. In some non-limiting embodiments or aspects, first mating element 410a may be the same as or similar to first mating element 110a. In some non-limiting embodiments or aspects, second medical device component 402b may be the same as or similar to second medical device component 102b. In some non-limiting embodiments or aspects, second resonant structure 404b may be the same as or similar to second resonant structure 104b. In some non-limiting embodiments or aspects, second metallic strip 406b may be the same as or similar to second metallic strip 406b. In some non-limiting embodiments or aspects, second antenna element 408b may be the same as or similar to second antenna element 408b. In some non-limiting embodiments or aspects, second mating element 410b may be the same as or similar to second mating element 110b.

In some non-limiting embodiments or aspects, first medical device component 402a may include a syringe, as described herein. Additionally or alternatively, second medical device component 402b may include a vascular access device (e.g., an IV line, a catheter, and/or the like), as described herein.

In some non-limiting embodiments or aspects, first medical device component 402a may include first antenna element 408a, as described herein. Additionally or alternatively, first antenna element 408a may have a resonant frequency spectrum, as described herein. For example, first antenna element 408a may include at least one first resonant structure 404a, and each first resonant structure 404a may have a resonant frequency spectrum (e.g., a first resonant frequency spectrum), as described herein. Additionally or alternatively, first antenna element 408a may include first metallic strip 406a, as described herein. In some non-limiting embodiments or aspects, first resonant structure 404a may include at least one spiral resonator (e.g., a first spiral resonator), as described herein. Additionally or alternatively, the first resonant frequency spectrum may include a first natural frequency of the first spiral resonator, as described herein.

In some non-limiting embodiments or aspects, upon interrogation of first medical device component 402a with an interrogation signal, first antenna element 408a (e.g., first resonant structure 404a thereof) may attenuate at least one first frequency component to form a first attenuated electromagnetic signal (e.g., a first reflected signal), as described herein. For example, the interrogation signal may include a multi-frequency electromagnetic signal, and upon interrogation of first medical device component 402a with the multi-frequency electromagnetic signal, first antenna element 408a (e.g., first resonant structure 404a thereof) may attenuate at least one first frequency component of the multi-frequency electromagnetic signal corresponding to the first resonant frequency spectrum to form the first attenuated electromagnetic signal, as described herein.

In some non-limiting embodiments or aspects, first medical device component 402a may include first mating element 410a, as described herein. For example, first mating element 410a may include a male luer fitting, as described herein.

In some non-limiting embodiments or aspects, second medical device component 402b may include second antenna element 408b, as described herein. Additionally or alternatively, second antenna element 408b may have a resonant frequency spectrum, as described herein. For example, second antenna element 408b may include at least one second resonant structure 404b, and each second resonant structure 404b may have a resonant frequency spectrum (e.g., a second resonant frequency spectrum), as described herein. Additionally or alternatively, second antenna element 408b may include second metallic strip 406b, as described herein. In some non-limiting embodiments or aspects, second resonant structure 404b may include at least one spiral resonator (e.g., a second spiral resonator), as described herein. Additionally or alternatively, the second resonant frequency spectrum may include a second natural frequency of the second spiral resonator, as described herein.

In some non-limiting embodiments or aspects, upon interrogation of second medical device component 402b with an interrogation signal, second antenna element 408b (e.g., second resonant structure 404b thereof) may attenuate at least one second frequency component to form a second attenuated electromagnetic signal (e.g., a second reflected signal), as described herein. For example, the interrogation signal may include a multi-frequency electromagnetic signal, and upon interrogation of second medical device component 402b with the multi-frequency electromagnetic signal, second antenna element 408b (e.g., second resonant structure 404b thereof) may attenuate at least one second frequency component of the multi-frequency electromagnetic signal corresponding to the second resonant frequency spectrum to form the second attenuated electromagnetic signal, as described herein.

In some non-limiting embodiments or aspects, second medical device component 402b may include second mating element 410b, as described herein. For example, second mating element 410b may include a female luer fitting, as described herein.

In some non-limiting embodiments or aspects, upon mating of first medical device component 402a (e.g., first mating element 410a thereof) to second medical device component 402b (e.g., second mating element 410b thereof), first antenna element 408a (e.g., first resonant structure 404a thereof) and second antenna element 408b (e.g., second resonant structure 404b thereof) may combine to have a third resonant frequency spectrum, as described herein. Additionally or alternatively, the third resonant frequency spectrum may be different than the first resonant frequency spectrum and the second resonant frequency spectrum, as described herein.

In some non-limiting embodiments or aspects, upon interrogation of the mated medical device components (e.g., first medical device component 402 and medical device component 402b upon mating) with an interrogation signal, the antenna elements thereof (e.g., first antenna element 408a (e.g., first resonant structure 404a thereof) and second antenna element 408b (e.g., second resonant structure 404b thereof)) may attenuate at least one third frequency component to form a third attenuated electromagnetic signal (e.g., a third reflected signal), as described herein.

Figure 5:
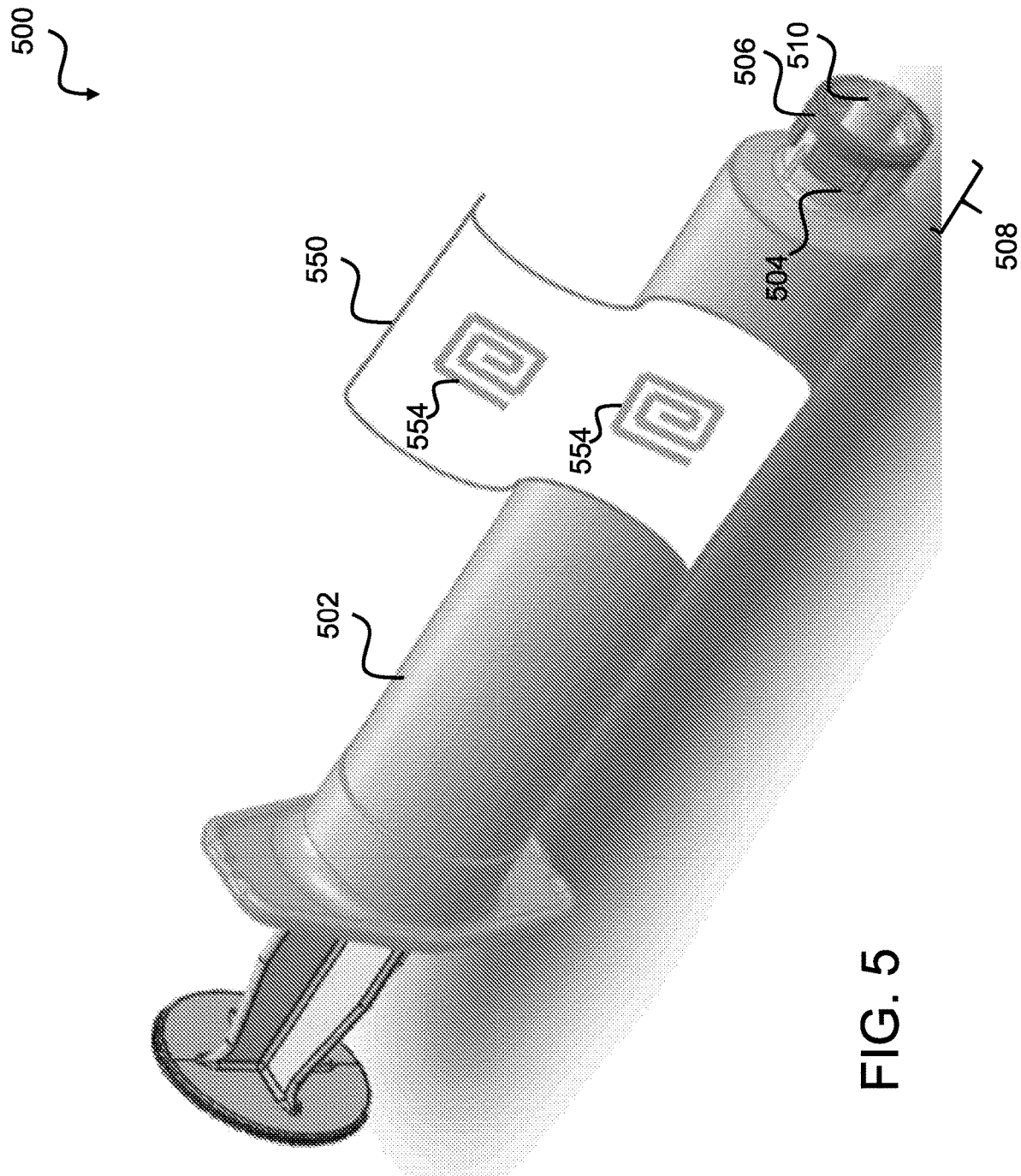
FIG. 5 is a diagram of a non-limiting embodiment or aspect of an implementation of one or more systems and/or one or more devices of FIG. 1 according to the principles of the presently disclosed subject matter.

Referring now to FIG. 5, FIG. 5 is a diagram of an exemplary implementation 500 of a non-limiting embodiment or aspect relating to environment 100 shown in FIG. 1. As shown in FIG. 5, implementation 500 may include medical device component 502, resonant structure 504, metallic strip 506, antenna element 508, mating element 510, tag 550, and/or tag resonant structure 554. In some non-limiting embodiments or aspects, medical device component 502 may be the same as or similar to first medical device component 102a and/or second medical device component 102b. In some non-limiting embodiments or aspects, resonant structure 504 may be the same as or similar to first resonant structure 104a and/or second resonant structure 104b. In some non-limiting embodiments or aspects, metallic strip 506 may be the same as or similar to first metallic strip 106a and/or second metallic strip 106b. In some non-limiting embodiments or aspects, antenna element 508 may be the same as or similar to first antenna element 108a and/or second antenna element 108b. In some non-limiting embodiments or aspects, mating element 510 may be the same as or similar to first mating element 110a and/or second mating element 110b. In some non-limiting embodiments or aspects, tag resonant structure 554 each may be the same as or similar to first resonant structure 104a and/or second resonant structure 104b.

In some non-limiting embodiments or aspects, medical device component 502 may include a syringe, as described herein.

In some non-limiting embodiments or aspects, medical device component 502 may include at least one antenna element, e.g., antenna element 508, tag 550 (and/or tag resonant structures thereof), any combination thereof, and/or the like.

In some non-limiting embodiments or aspects, antenna element 508 may have a resonant frequency spectrum, as described herein. For example, antenna element 508 may include at least one resonant structure 504, and each resonant structure 504 may have a resonant frequency spectrum (e.g., a first resonant frequency spectrum), as described herein. Additionally or alternatively, antenna element 508 may include metallic strip 506, as described herein. In some non-limiting embodiments or aspects, resonant structure 504 may include at least one spiral resonator (e.g., a first spiral resonator), as described herein. Additionally or alternatively, the first resonant frequency spectrum may include a first natural frequency of the first spiral resonator, as described herein.

In some non-limiting embodiments or aspects, tag 550 may have a resonant frequency spectrum. Additionally or alternatively, tag 550 may include at least one tag resonant structure 554, and each tag resonant structure 554 may have a resonant frequency spectrum (e.g., a second resonant frequency spectrum), as described herein.

In some non-limiting embodiments or aspects, tag resonant structure 554 may include at least one spiral resonator (e.g., a second spiral resonator), as described herein. Additionally or alternatively, the second resonant frequency spectrum may include a second natural frequency of the second spiral resonator, as described herein.

In some non-limiting embodiments or aspects, medical device component 502 may include tag 550 in addition to antenna element 508. Additionally or alternatively, medical device component 502 may include tag 550 in lieu of (e.g., without, independent of, and/or the like) antenna element 508.

In some non-limiting embodiments or aspects, upon interrogation of medical device component 502 with an interrogation signal, antenna element 508 (e.g., resonant structure 504 thereof) may attenuate at least one first frequency component to form a first attenuated electromagnetic signal (e.g., first reflected signal), as described herein. For example, the interrogation signal may include a multi-frequency electromagnetic signal, and upon interrogation of medical device component 502 with the multi-frequency electromagnetic signal, antenna element 508 (e.g., resonant structure 504 thereof) may attenuate at least one first frequency component of the multi-frequency electromagnetic signal corresponding to the first resonant frequency spectrum to form the first attenuated electromagnetic signal, as described herein.

In some non-limiting embodiments or aspects, upon interrogation of medical device component 502 with an interrogation signal, tag 550 (e.g., tag resonant structure 554 thereof) may attenuate at least one second frequency component to form a second attenuated electromagnetic signal (e.g., second reflected signal), as described herein. For example, the interrogation signal may include a multi-frequency electromagnetic signal, and upon interrogation of medical device component 502 with the multi-frequency electromagnetic signal, tag 550 (e.g., tag resonant structure 554 thereof) may attenuate at least one second frequency component of the multi-frequency electromagnetic signal corresponding to the second resonant frequency spectrum to form the second attenuated electromagnetic signal, as described herein.

In some non-limiting embodiments or aspects, medical device component 502 may include mating element 510, as described herein. For example, mating element 510 may include a male luer fitting, a female luer fitting, any combination thereof, and/or the like, as described herein.

In some non-limiting embodiments or aspects, upon mating of medical device component 502 (e.g., mating element 510 thereof) to a second medical device component (e.g., a second mating element thereof), antenna element 508 (e.g., resonant structure 504 thereof) may combine with a second antenna element of the second medical device component (e.g., a second resonant structure thereof) to have a third resonant frequency spectrum, as described herein. Additionally or alternatively, the third resonant frequency spectrum may be different than the first resonant frequency spectrum and the second resonant frequency spectrum, as described herein. In some non-limiting embodiments or aspects, upon interrogation of the mated medical device components with an interrogation signal, the antenna elements thereof may attenuate at least one third frequency component to form a third attenuated electromagnetic signal (e.g., third reflected signal), as described herein.

In some non-limiting embodiments or aspects, tag 550 may include a substrate, as described herein. Additionally or alternatively, the substrate (e.g., of tag 550) may include (e.g., be formed of and/or the like) a dielectric material (e.g., plastic, flexible polymer, polypropylene, polyethylene terephthalate (PET), paper, and/or the like). In some non-limiting embodiments or aspects, tag 550 may be affixed to medical device component 502, as described herein.

In some non-limiting embodiments or aspects, the at least one tag resonant structure 554 may include a plurality of tag resonant structures 554, as described herein. In some non-limiting embodiments or aspects, the plurality of tag resonant structures 554 (and/or a subset thereof) may be disposed circumferentially around medical device component 502, as described herein. Additionally or alternatively, each of the plurality of tag resonant structures 554 (and/or a subset thereof) may be disposed longitudinally (e.g., axially, parallel to the axis of, and/or the like) along medical device component 502, as described herein.

Figure 6A:
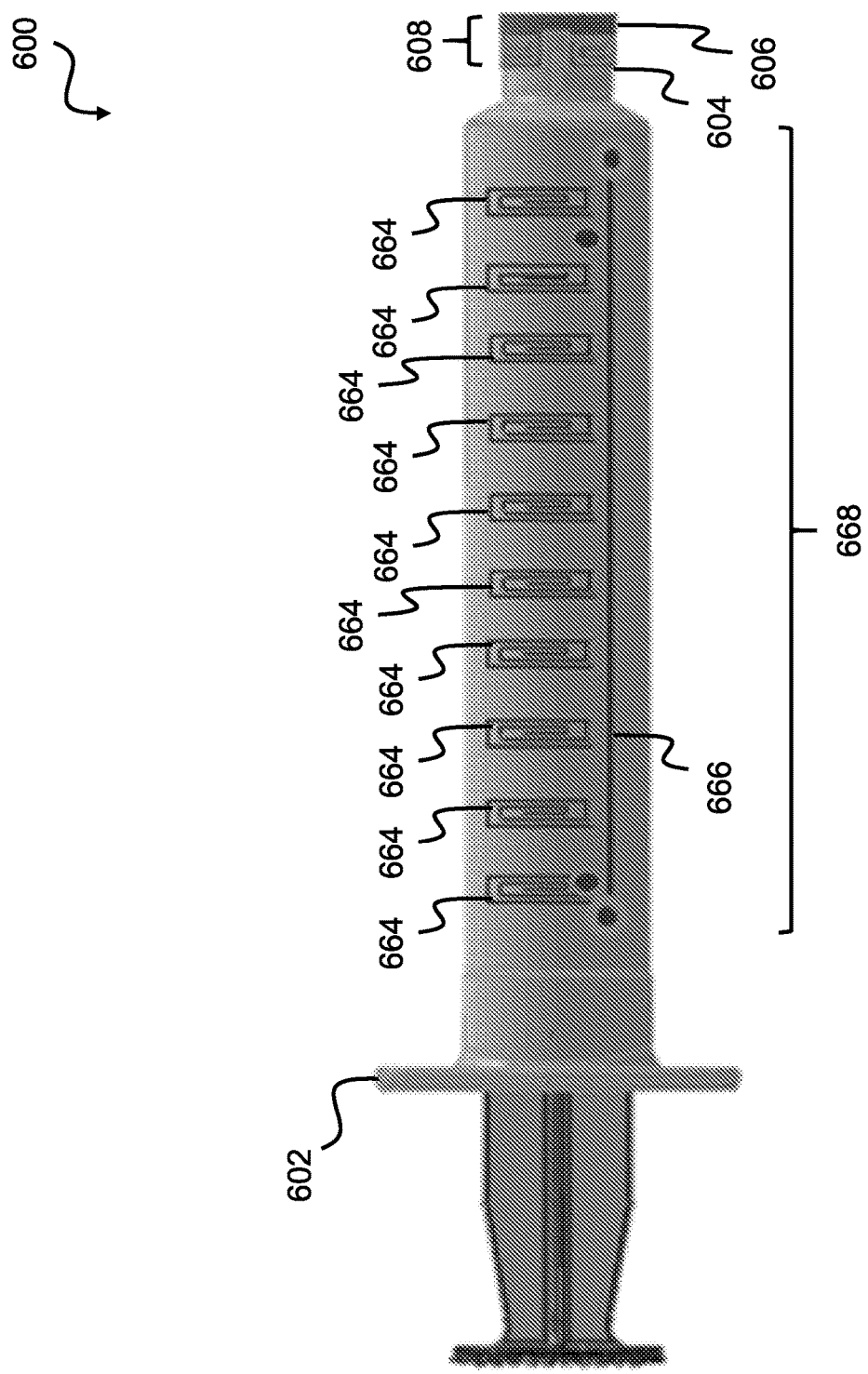
FIG. 6A is a diagram of a non-limiting embodiment or aspect of an implementation of one or more systems and/or one or more devices of FIG. 1 according to the principles of the presently disclosed subject matter.

Referring now to FIG. 6A, FIG. 6A is a diagram of an exemplary implementation 600 of a non-limiting embodiment or aspect relating to environment 100 shown in FIG. 1. As shown in FIG. 6A, implementation 600 may include medical device component 602, resonant structure 604, metallic strip 606, antenna element 608, scale marking resonant structure 664, longitudinal metallic strip 666, and/or longitudinal antenna element 668. In some non-limiting embodiments or aspects, medical device component 602 may be the same as or similar to first medical device component 102a and/or second medical device component 102b. In some non-limiting embodiments or aspects, resonant structure 604 may be the same as or similar to first resonant structure 104a and/or second resonant structure 104b. In some non-limiting embodiments or aspects, metallic strip 606 may be the same as or similar to first metallic strip 106a and/or second metallic strip 106b. In some non-limiting embodiments or aspects, antenna element 608 may be the same as or similar to first antenna element 108a and/or second antenna element 108b. In some non-limiting embodiments or aspects, scale marking resonant structure 664 may be the same as or similar to first resonant structure 104a and/or second resonant structure 104b. In some non-limiting embodiments or aspects, longitudinal metallic strip 666 may be the same as or similar to first metallic strip 106a and/or second metallic strip 106b. In some non-limiting embodiments or aspects, longitudinal antenna element 668 may be the same as or similar to first antenna element 108a and/or second antenna element 108b.

In some non-limiting embodiments or aspects, medical device component 602 may include a syringe, as described herein.

In some non-limiting embodiments or aspects, medical device component 602 may include at least one antenna element, e.g., antenna element 608, longitudinal antenna element 668, any combination thereof, and/or the like.

In some non-limiting embodiments or aspects, antenna element 608 may have a resonant frequency spectrum, as described herein. For example, antenna element 608 may include at least one resonant structure 604, and each resonant structure 604 may have a resonant frequency spectrum (e.g., a first resonant frequency spectrum), as described herein. Additionally or alternatively, antenna element 608 may include metallic strip 606, as described herein. In some non-limiting embodiments or aspects, resonant structure 604 may include at least one spiral resonator (e.g., a first spiral resonator), as described herein. Additionally or alternatively, the first resonant frequency spectrum may include a first natural frequency of the first spiral resonator, as described herein.

In some non-limiting embodiments or aspects, longitudinal antenna element 668 may have a resonant frequency spectrum, as described herein. Additionally or alternatively, longitudinal antenna element 668 may include at least one scale marking resonant structure 664, and each scale marking resonant structure 664 may have a resonant frequency spectrum (e.g., a second resonant frequency spectrum), as described herein. Additionally or alternatively, longitudinal antenna element 668 may include longitudinal metallic strip 666, as described herein. In some non-limiting embodiments or aspects, scale marking resonant structure 664 may include at least one spiral resonator (e.g., a second spiral resonator), as described herein. Additionally or alternatively, the second resonant frequency spectrum may include a second natural frequency of the second spiral resonator, as described herein.

In some non-limiting embodiments or aspects, longitudinal metallic strip 666 (e.g., at least a portion thereof) may be disposed longitudinally (e.g., axially, parallel to the axis of, and/or the like) along medical device component 602, as described herein. In some non-limiting embodiments or aspects, the at least one scale marking resonant structure 664 may include a plurality of scale marking resonant structures 664, as described herein. In some non-limiting embodiments or aspects, the plurality of scale marking resonant structures 664 (and/or a subset thereof) may be disposed longitudinally (e.g., axially, parallel to the axis of, and/or the like) along medical device component 602, as described herein. For example, each scale marking resonant structure 664 (and/or each of a subset thereof) may be disposed at a distinct scale marking on medical device component 602, as described herein. In some non-limiting embodiments or aspects, each of the plurality of scale marking resonant structures 664 may include (e.g., be formed of and/or the like) a conductive ink, as described herein.

In some non-limiting embodiments or aspects, medical device component 602 may include longitudinal antenna element 668 in addition to antenna element 608. Additionally or alternatively, medical device component 602 may include longitudinal antenna element 668 in lieu of (e.g., without, independent of, and/or the like) antenna element 608.

In some non-limiting embodiments or aspects, upon interrogation of medical device component 602 with an interrogation signal, antenna element 608 (e.g., resonant structure 604 thereof) may attenuate at least one first frequency component to form a first attenuated electromagnetic signal (e.g., first reflected signal), as described herein. For example, the interrogation signal may include a multi-frequency electromagnetic signal, and upon interrogation of medical device component 602 with the multi-frequency electromagnetic signal, antenna element 608 (e.g., resonant structure 604 thereof) may attenuate at least one first frequency component of the multi-frequency electromagnetic signal corresponding to the first resonant frequency spectrum to form the first attenuated electromagnetic signal, as described herein.

In some non-limiting embodiments or aspects, upon interrogation of medical device component 602 with an interrogation signal, longitudinal antenna element 668 (e.g., scale marking resonant structure 664 thereof) may attenuate at least one second frequency component to form a second attenuated electromagnetic signal (e.g., second reflected signal), as described herein. For example, the interrogation signal may include a multi-frequency electromagnetic signal, and upon interrogation of medical device component 602 with the multi-frequency electromagnetic signal, longitudinal antenna element 668 (e.g., scale marking resonant structure 664 thereof) may attenuate at least one second frequency component of the multi-frequency electromagnetic signal corresponding to the second resonant frequency spectrum to form the second attenuated electromagnetic signal, as described herein.

In some non-limiting embodiments or aspects, upon mating of medical device component 602 (e.g., mating element 610 thereof) to a second medical device component (e.g., a second mating element thereof), antenna element 608 (e.g., resonant structure 604 thereof) may combine with a second antenna element of the second medical device component (e.g., a second resonant structure thereof) to have a third resonant frequency spectrum, as described herein. Additionally or alternatively, the third resonant frequency spectrum may be different than the first resonant frequency spectrum and the second resonant frequency spectrum, as described herein. In some non-limiting embodiments or aspects, upon interrogation of the mated medical device components with an interrogation signal, the antenna elements thereof may attenuate at least one third frequency component to form a third attenuated electromagnetic signal (e.g., third reflected signal), as described herein.

Figure 6C:
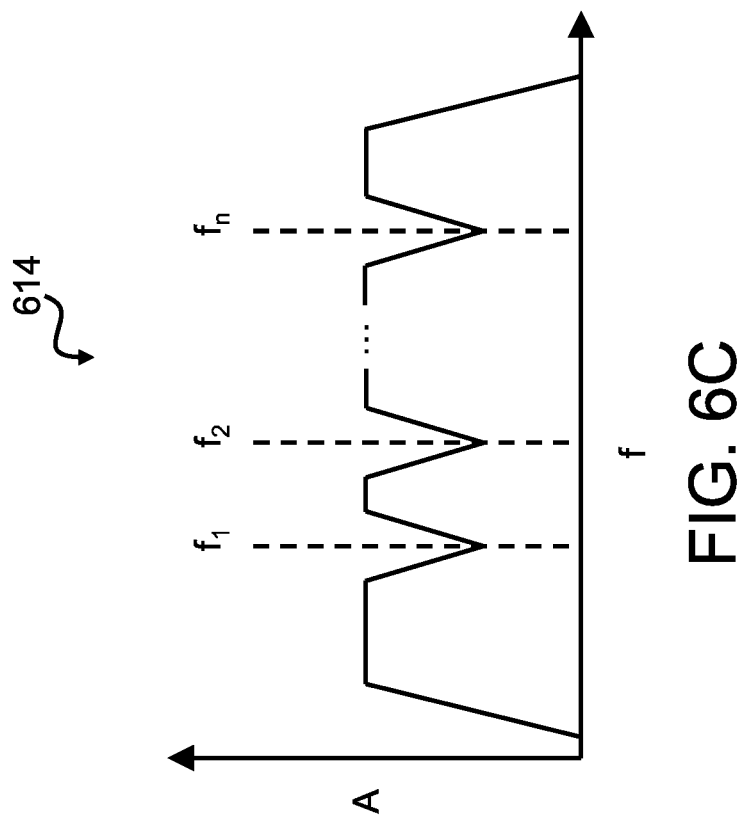
FIG. 6C is a graph of a non-limiting embodiment or aspect of frequency spectra of an implementation of one or more systems and/or one or more devices of FIGS. 1 and 6A according to the principles of the presently disclosed subject matter.
Figure 6B:
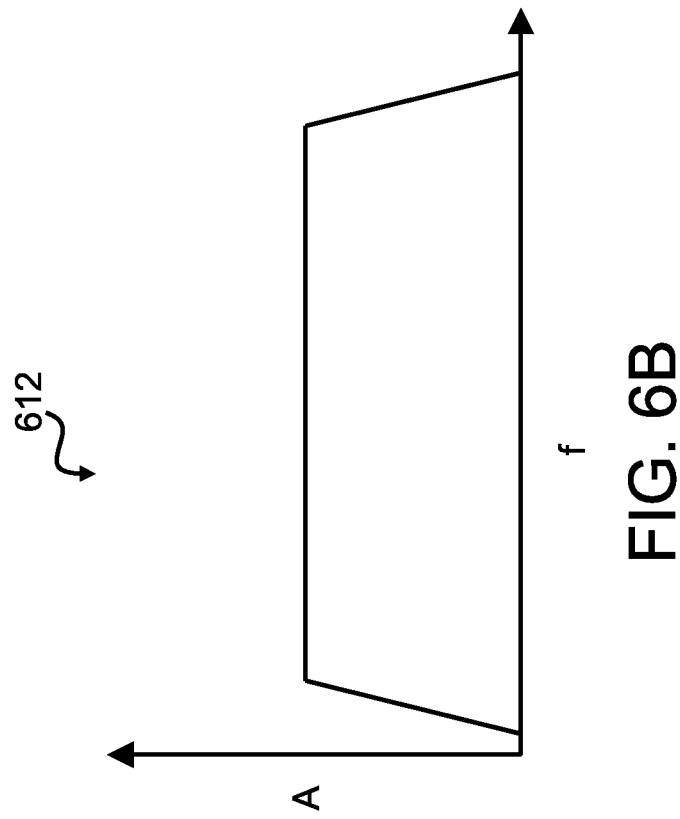
FIG. 6B is a graph of a non-limiting embodiment or aspect of frequency spectra of an implementation of one or more systems and/or one or more devices of FIGS. 1 and 6A according to the principles of the presently disclosed subject matter.

Referring now to FIGS. 6B and 6C, FIGS. 6B and 6C are graphs of exemplary frequency spectra of an implementation of a non-limiting embodiment or aspect relating to implementation 600 shown in FIG. 6A. As shown in FIGS. 6B and 6C, a graph may have a horizontal axis associated with frequency (f) and a vertical axis associated with amplitude (A).

Referring to FIG. 6B, interrogation signal 612 may include a multi-frequency electromagnetic signal, as described herein. For example, interrogation signal 612 may include a continuous wave, multi-frequency electromagnetic signal of uniform amplitude and phase across a range of frequencies. In some non-limiting embodiments or aspects, interrogation signal 612 may be the same as or similar to interrogation signal 112.

Referring to in FIG. 6C, second reflected signal 614 may include the second attenuated electromagnetic signal from longitudinal antenna element 668, as described herein. For example, second reflected signal 614 may include at least one of an amplitude attenuation, a phase jump, a frequency attenuation, any combination thereof, and/or the like corresponding to a second resonant frequency spectrum (e.g., associated with longitudinal antenna element 668 and/or scale marking resonant structure(s) 664 thereof), as described herein. For the purpose of illustration, as shown in FIG. 6C, second reflected signal 614 may include an amplitude attenuation around a natural frequency of each of a plurality of scale marking resonant structures 664. For example, second reflected signal 614 may include a first amplitude attenuation around a first natural frequency $f_1$ (e.g., associated with a first scale marking resonant structure 664 and/or the like), a second amplitude attenuation around a second natural frequency $f_2$ (e.g., associated with a second scale marking resonant structure 664 and/or the like), an nth amplitude attenuation around an nth natural frequency $f_n$ (e.g., associated with an nth scale marking resonant structure 664 and/or the like), any combination thereof, and/or the like.

In some non-limiting embodiments or aspects, each type of medical device component (e.g., first medical device component 102a, second medical device component 102b, and/or the like, as described herein) may have a unique identifier (e.g., stock keeping unit (SKU) and/or the like). Additionally or alternatively, each of N possible scale marking resonant structures 664 may have a unique natural frequency. In some non-limiting embodiments or aspects, each respective type of medical device component may be uniquely identified based on a unique subset of up to n scale marking resonant structures 664 (e.g., where n may be less than or equal to N). For example, each of the N possible scale marking resonant structures 664 may be associated with one bit, and if a respective subset includes a respective one of the N possible scale marking resonant structures 664 (e.g., if the second reflected signal 614 includes the natural frequency of the respective one of the N possible scale marking resonant structures 664), the presence the respective one of the N possible scale marking resonant structures 664 may be associated with a first logical value (e.g., 1, 0, and/or the like). Additionally or alternatively, if a respective subset does not include a respective one of the N possible scale marking resonant structures 664 (e.g., if the second reflected signal 614 does not include the natural frequency of the respective one of the N possible scale marking resonant structures 664), the absence of the respective one of the N possible scale marking resonant structures 664 may be associated with a second logical value (e.g., 0, 1, and/or the like, respectively). Thus, each unique natural frequency may be the same as or similar to a logical bit (e.g., the bit may be 1 (present), 0 (absent), and/or the like). In some non-limiting embodiments or aspects, each possible permutation of subsets of up to n scale marking resonant structures 664 may be associated with a number including multiple bits, with each bit associated with a 1 (e.g., respective natural frequency present) or 0 (respective natural frequency absent) and/or the like. Additionally or alternatively, each possible permutation of subsets of up to n scale marking resonant structures 664 (e.g., the number including multiple bits associated therewith and/or the like) may be associated with a respective one of the unique identifiers for the plurality of types of medical device components. In some non-limiting embodiments or aspects, a mapping (e.g., database, table, and/or the like) may be stored (e.g., by server 130 and/or the like), and the mapping may map each type of medical device component (e.g., the unique identifier thereof) to the respective possible permutation of a subset of up to n scale marking resonant structures 664 (e.g., the number including multiple bits associated therewith and/or the like). In some non-limiting embodiments or aspects, the total number of possible bits may be up to 35 bits. Additionally or alternatively, the density of bits per unit may include up to 5.88 bits/cm 2, up to 5.22 bits/cm 2, up to 4.17 bits/cm 2, up to 3.56 bits/cm 2, up to 3 bits/cm 2, up to 2.86 bits/cm 2, up to 2.37 bits/cm 2, up to 2.11 bits/cm 2, up to 1.25 bits/cm 2, up to 1.14 bits/cm 2, up to 0.77 bits/cm 2, up to 0.61 bits/cm 2, up to 0.2 bits/cm 2, up to 0.1 bits/cm 2, and/or the like (e.g., based on the geometric properties of resonant structures 664, material properties of resonant structures 664, operating frequencies of resonant structures 664, and/or the like).

Figure 7:
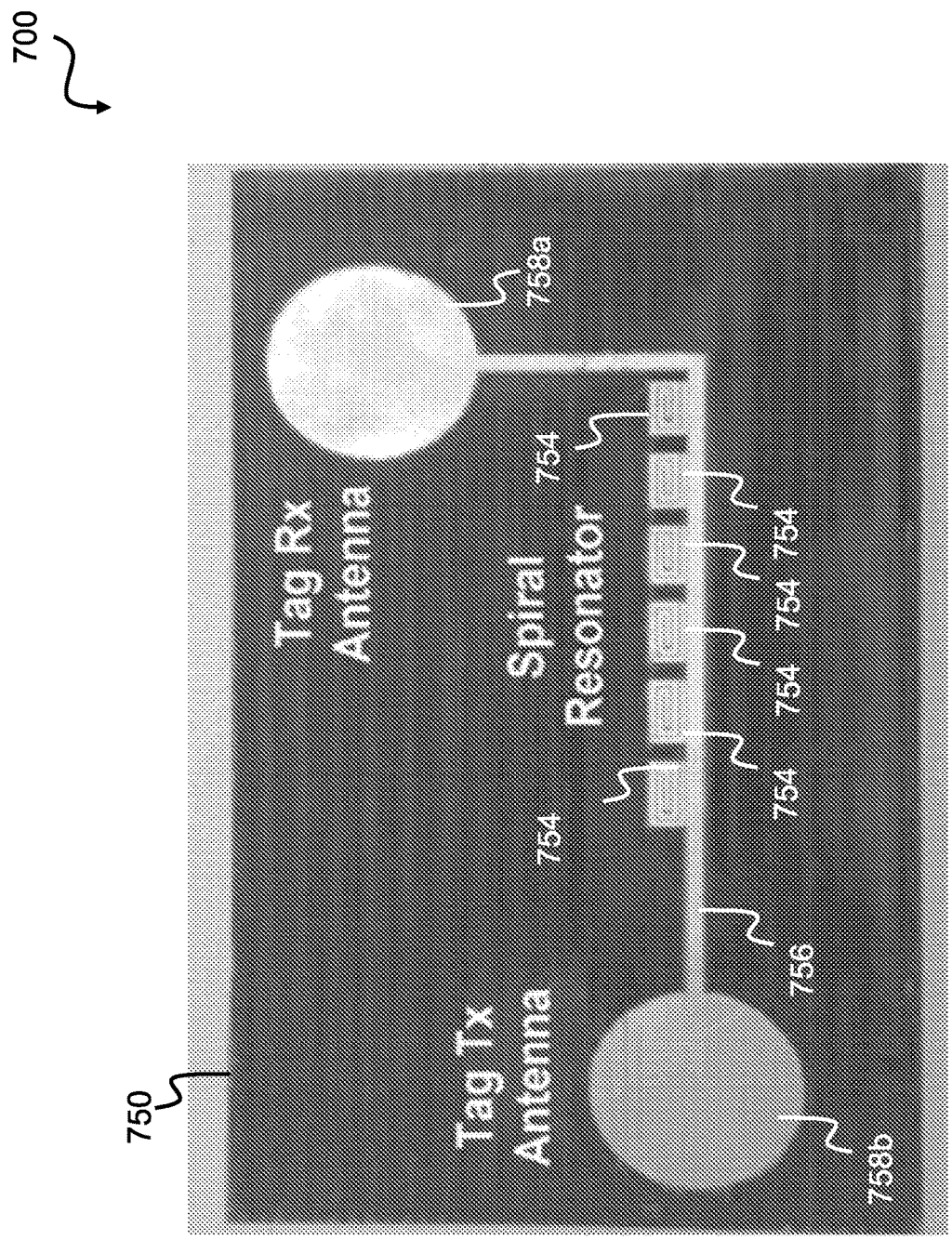
FIG. 7 is a diagram of a non-limiting embodiment or aspect of an implementation of one or more systems and/or one or more devices of FIG. 1 according to the principles of the presently disclosed subject matter.

Referring now to FIG. 7, FIG. 7 is a diagram of an exemplary implementation 700 of a non-limiting embodiment or aspect relating to environment 100 shown in FIG. 1. As shown in FIG. 7, implementation 700 may include tag 750, tag resonant structure 754, tag metallic strip 756, first tag antenna element 758a, and/or second tag antenna element 758b. In some non-limiting embodiments or aspects, tag 750 may be affixed to a medical device component (e.g., first medical device component 102a and/or second medical device component 102b). Additionally or alternatively, tag 750 may be the same as or similar to tag 550. In some non-limiting embodiments or aspects, tag resonant structure 754 may be the same as or similar to first resonant structure 104a and/or second resonant structure 104b. In some non-limiting embodiments or aspects, tag metallic strip 756 may be the same as or similar to first metallic strip 106a and/or second metallic strip 106b. In some non-limiting embodiments or aspects, first tag antenna element 758a may be the same as or similar to first antenna element 108a (e.g., first transmitting antenna element thereof) and/or second antenna element 108b (e.g., a second transmitting antenna element thereof). In some non-limiting embodiments or aspects, second tag antenna element 758b may be the same as or similar to first antenna element 108a (e.g., first receiving antenna element thereof) and/or second antenna element 108b (e.g., second receiving antenna element thereof).

In some non-limiting embodiments or aspects, tag 750 may have a resonant frequency spectrum. Additionally or alternatively, tag 750 may include at least one tag resonant structure 754, and each tag resonant structure 754 may have a resonant frequency spectrum, as described herein. In some non-limiting embodiments or aspects, each tag resonant structure 754 may include at least one spiral resonator, as described herein. Additionally or alternatively, the resonant frequency spectrum may include a natural frequency of the spiral resonator, as described herein.

In some non-limiting embodiments or aspects, upon interrogation of tag 750 with an interrogation signal, tag 750 (e.g., tag resonant structure 554 thereof) may attenuate at least one frequency component to form an attenuated electromagnetic signal (e.g., reflected signal), as described herein. For example, the interrogation signal may include a multi-frequency electromagnetic signal, and upon interrogation of tag 750 with the multi-frequency electromagnetic signal, tag 750 (e.g., tag resonant structure 754 thereof) may attenuate at least one frequency component of the multi-frequency electromagnetic signal corresponding to the resonant frequency spectrum to form the second attenuated electromagnetic signal, as described herein.

In some non-limiting embodiments or aspects, tag 750 may include a substrate, as described herein. Additionally or alternatively, the substrate (e.g., of tag 750) may include (e.g., be formed of and/or the like) a dielectric material (e.g., plastic, flexible polymer, polypropylene, polyethylene terephthalate (PET), paper, and/or the like). In some non-limiting embodiments or aspects, tag 750 may be affixed to a medical device component, as described herein.

In some non-limiting embodiments or aspects, the at least one tag resonant structure 754 may include a plurality of tag resonant structures 754, as described herein. In some non-limiting embodiments or aspects, the plurality of tag resonant structures 754 (and/or a subset thereof) may be disposed longitudinally (e.g., axially, parallel to the axis of, and/or the like) along a medical device component (e.g., when tag 750 is affixed to the medical device component and/or the like), as described herein.

In some non-limiting embodiments or aspects, tag 750 may include first tag antenna element 758a (e.g., a receiving antenna element) and/or second tag antenna element 758b (e.g. a transmitting antenna element) and/or the like. For example, each of first tag antenna element 758a (e.g., a receiving antenna element) and/or second tag antenna element 758b (e.g. a transmitting antenna element) may include a disc-shaped metallic conductor. Additionally or alternatively, the first tag antenna element 758a (e.g., a receiving antenna element) and/or second tag antenna element 758b (e.g. a transmitting antenna element) may be attached at opposite ends of tag metallic strip 756. In some non-limiting embodiments or aspects, the first tag antenna element 758a (e.g., a receiving antenna element) and second tag antenna element 758b (e.g. a transmitting antenna element) may be cross-polarized. For example, first tag antenna element 758a (e.g., a receiving antenna element) and second tag antenna element 758b (e.g. a transmitting antenna element) may be arranged (e.g., disposed and/or the like) on tag 750 such that, when tag 750 is affixed to a medical device component (e.g., wrapped around a cylindrical medical device component and/or the like), first tag antenna element 758a (e.g., a receiving antenna element) may be oriented orthogonally to second tag antenna element 758b (e.g. a transmitting antenna element). For example, first tag antenna element 758a (e.g., a surface thereof) may be disposed in (e.g., substantially in, predominantly in, and/or the like) a first plane and second tag antenna element 758b (e.g., a surface thereof) may be disposed in (e.g., substantially in, predominantly in, and/or the like) a second plane orthogonal to the first plane.

Figure 8:
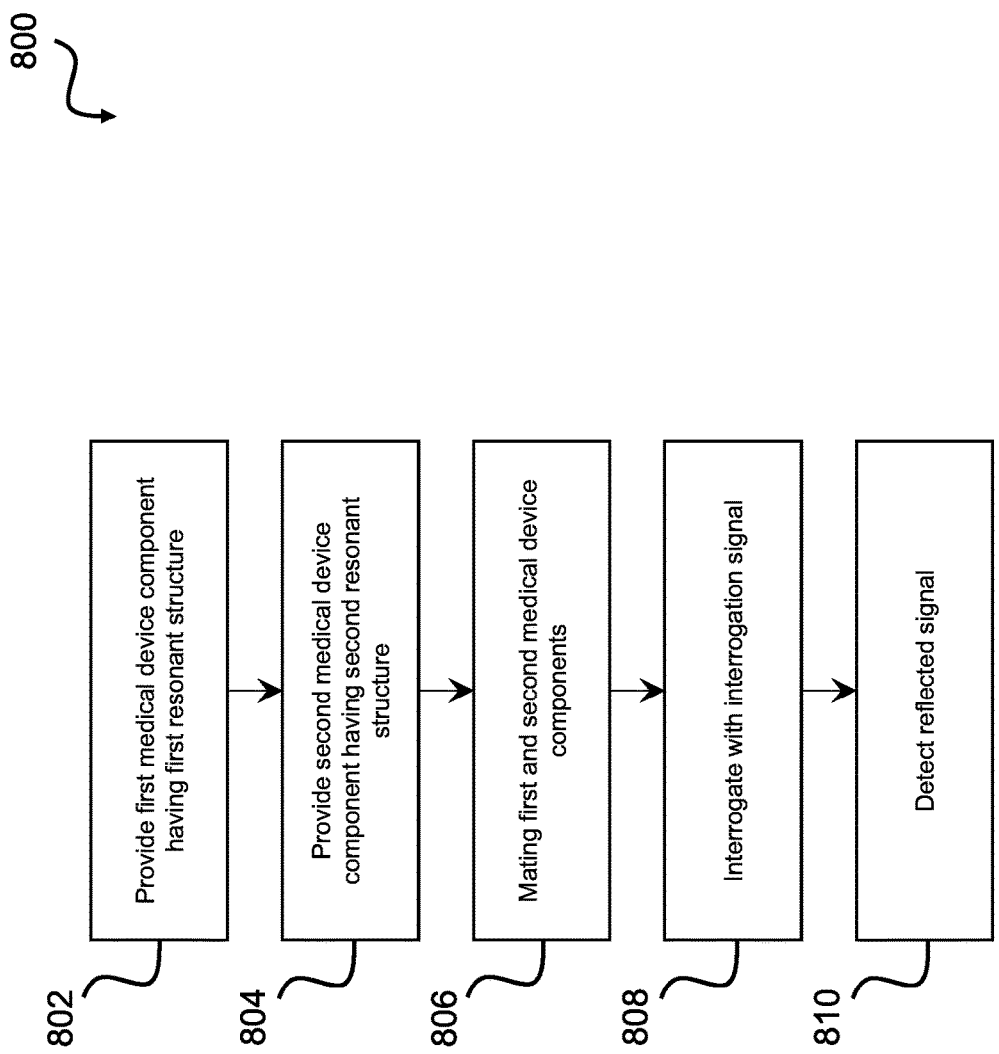
FIG. 8 is a flowchart of non-limiting embodiments or aspects of a process for detecting mating of medical device components according to the principles of the presently disclosed subject matter.

Referring now to FIG. 8, FIG. 8 is a flowchart of a non-limiting embodiment or aspect of a process 800 for detecting mating of medical device components. In some non-limiting embodiments or aspects, one or more of the steps of process 800 may be performed (e.g., completely, partially, and/or the like) by reader device 120 (e.g., one or more devices of reader device 120, such as generator 122, reader 124, and/or the like). In some non-limiting embodiments or aspects, one or more of the steps of process 800 may be performed (e.g., completely, partially, and/or the like) by another system, another device, another group of systems, or another group of devices, separate from or including reader device 120, such as medical device assembly 102 (e.g., one or more components of medical device assembly 102, such as first medical device component 102a, second medical device component 102b, and/or the like), server 130 (e.g., one or more devices of server 130), and/or the like.

As shown in FIG. 8, at step 802, process 800 may include providing a first medical device component. For example, first medical device component 102a may be provided. Additionally or alternatively, first medical device component 102a may have at least one first resonant structure 104a, as described herein. In some non-limiting embodiments or aspects, first resonant structure 104a may have a first resonant frequency spectrum, as described herein.

As shown in FIG. 8, at step 804, process 800 may include providing a second medical device component. For example, second medical device component 102b may be provided. Additionally or alternatively, second medical device component 102b may have at least one second resonant structure 104b, as described herein. In some non-limiting embodiments or aspects, second resonant structure 104b may have a second resonant frequency spectrum. In some non-limiting embodiments or aspects, the second resonant frequency spectrum may be the same as the first resonant frequency spectrum, as described herein. In some non-limiting embodiments or aspects, the second resonant frequency spectrum may be different than the first resonant frequency spectrum, as described herein.

As shown in FIG. 8, at step 806, process 800 may include mating the first and second medical device components. For example, first medical device component 102a and second medical device component 102b may be mated to form a medical device assembly (e.g., medical device assembly 102), as described herein. In some non-limiting embodiments or aspects, upon mating, first resonant structure 104*a* and second resonant structure 104*b* may combine (e.g., electromagnetically couple and/or the like) to have a third resonant frequency spectrum, as described herein. Additionally or alternatively, the third resonant frequency spectrum may be different than the first resonant frequency spectrum and the second resonant frequency spectrum, as described herein.

As shown in FIG. 8, at step 808, process 800 may include interrogating the medical device assembly with an interrogation signal. For example, reader device 120 and/or generator 122 may interrogate medical device assembly 102 with interrogation signal 112, as described herein. For example, reader device 120 and/or generator 122 may transmit interrogation signal 112 (e.g., to the medical device assembly 102), as described herein. In some non-limiting embodiments or aspects, interrogation signal 112 may include a multi-frequency electromagnetic signal, as described herein.

As shown in FIG. 8, at step 810, process 800 may include detecting a reflected signal. For example, reader device 120 and/or reader 124 may detect a reflected signal (e.g., third reflected signal 114*c*) from medical device assembly 102, as described herein. In some non-limiting embodiments or aspects, the reflected signal (e.g., third reflected signal 114*c*) may correspond to the third resonant frequency spectrum, as described herein.

In some non-limiting embodiments or aspects, upon interrogation of medical device assembly 102 with interrogation signal 112, at least one frequency component of interrogation signal 112 corresponding to the third resonant frequency spectrum may be attenuated to form the reflected signal (e.g., third reflected signal 114*c*), as described herein. In some non-limiting embodiments or aspects, detecting the reflected signal (e.g., third reflected signal 114*c*) may include receiving the reflected signal and detecting at least one of an amplitude attenuation, a phase jump, a frequency attenuation, any combination thereof, and/or the like in the reflected signal corresponding to the third resonant frequency spectrum, as described herein.

In some non-limiting embodiments or aspects, reader device 120 and/or reader 124 may detect a reflected signal (e.g., first reflected signal 114*a* and/or second reflected signal 114*b*) from medical device assembly 102, as described herein. In some non-limiting embodiments or aspects, the reflected signal (e.g., first reflected signal 114*a* and/or second reflected signal 114*b*) may correspond to the first and/or second resonant frequency spectrum, as described herein. Additionally or alternatively, upon detecting the reflected signal (e.g., first reflected signal 114*a* and/or second reflected signal 114*b*), reader device 120, reader 124, and/or server 130 may determine that first medical device component 102*a* and second medical device component 102*b* are not mated (e.g., were never successfully mated, disconnected such that the medical device components are no longer mated, and/or the like).

In some non-limiting embodiments or aspects, reflected signal data associated with the reflected signal may be stored. For example, reader device 120 and/or reader 124 may store reflected signal data associated with the reflected signal. Additionally or alternatively, reader device 120 and/or reader 124 may communicate the reflected signal data to server 130. In some non-limiting embodiments or aspects, server 130 may store reflected signal data associated with the reflected signal in a database, as described herein.

In some non-limiting embodiments or aspects, detecting the reflected signal may include detecting the reflected signal with one of a plurality of reader devices 120 and/or readers 124, as described herein. Additionally or alternatively, each reader device 120 and/or reader 124 may be disposed at a location within at least one site, as described herein. In some non-limiting embodiments or aspects, a location of medical device assembly 102 may be determined based on the location of the one of the plurality of reader devices 120 and/or readers 124.

In some non-limiting embodiments or aspects, compliance (e.g., compliant mating of first medical device component 102*a* and second medical device component 102*b*) may be determined (e.g., detected, monitored, and/or the like), as described herein.

Figure 9:
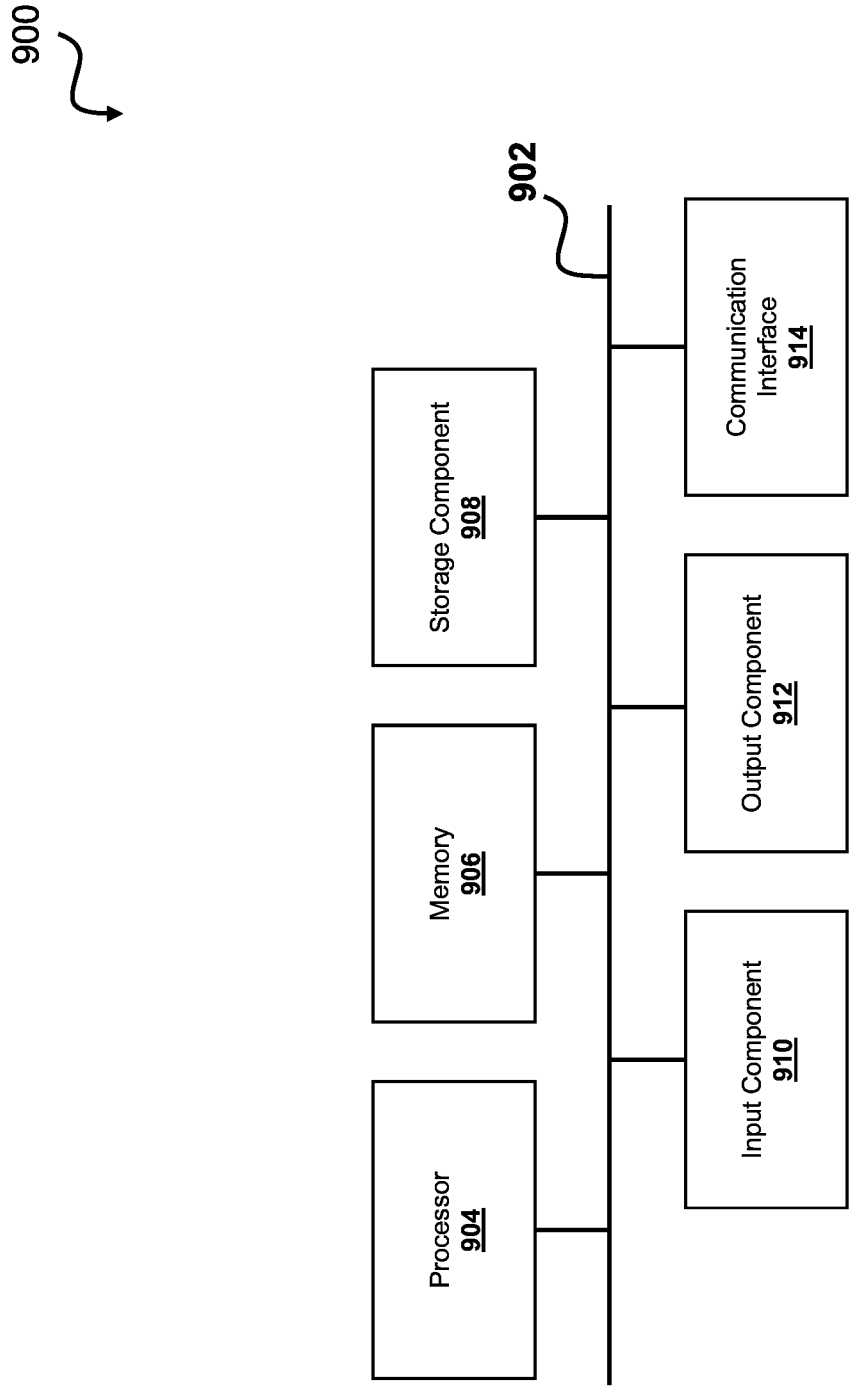
FIG. 9 is a diagram of non-limiting embodiments or aspects of components of one or more devices of FIG. 1.

Referring now to FIG. 9, FIG. 9 is a diagram of example components of a device 900. Device 900 may correspond to one or more devices of reader device 120, generator 122, reader 124, server 130, and/or network 140. In some non-limiting embodiments or aspects, reader device 120, generator 122, reader 124, server 130, and/or network 140 may include at least one device 900 and/or at least one component of device 900. As shown in FIG. 9, device 900 may include bus 902, processor 904, memory 906, storage component 908, input component 910, output component 912, and communication interface 914.

Bus 902 may include a component that permits communication among the components of device 900. In some non-limiting embodiments or aspects, processor 904 may be implemented in hardware, software, firmware, and/or any combination thereof. For example, processor 904 may include a processor (e.g., a central processing unit (CPU), a graphics processing unit (GPU), an accelerated processing unit (APU), and/or the like), a microprocessor, a digital signal processor (DSP), and/or any processing component (e.g., a field-programmable gate array (FPGA), an application-specific integrated circuit (ASIC), and/or the like), and/or the like, which can be programmed to perform a function. Memory 906 may include random access memory (RAM), read-only memory (ROM), and/or another type of dynamic or static storage device (e.g., flash memory, magnetic memory, optical memory, and/or the like) that stores information and/or instructions for use by processor 904.

Storage component 908 may store information and/or software related to the operation and use of device 900. For example, storage component 908 may include a hard disk (e.g., a magnetic disk, an optical disk, a magneto-optic disk, a solid state disk, and/or the like), a compact disc (CD), a digital versatile disc (DVD), a floppy disk, a cartridge, a magnetic tape, and/or another type of computer-readable medium, along with a corresponding drive.

Input component 910 may include a component that permits device 900 to receive information, such as via user input (e.g., a touch screen display, a keyboard, a keypad, a mouse, a button, a switch, a microphone, a camera, and/or the like). Additionally or alternatively, input component 910 may include an antenna for receiving electromagnetic radiation, a sensor for sensing information (e.g., a global positioning system (GPS) component, an accelerometer, a gyroscope, an actuator, and/or the like), and/or the like. Output component 912 may include a component that provides output information from device 900 (e.g., an antenna for transmitting electromagnetic radiation, a display, a speaker, one or more light-emitting diodes (LEDs), and/or the like).

Communication interface 914 may include a transceiver-like component (e.g., a transceiver, a receiver and transmitter that are separate, and/or the like) that enables device 900 to communicate with other devices, such as via a wired connection, a wireless connection, or a combination of wired and wireless connections. Communication interface 914 may permit device 900 to receive information from another device and/or provide information to another device. For example, communication interface 914 may include an Ethernet interface, an optical interface, a coaxial interface, an infrared interface, a radio frequency (RF) interface, a universal serial bus (USB) interface, a Wi-Fi® interface, a Bluetooth® interface, a Zigbee® interface, a cellular network interface, and/or the like.

Device 900 may perform one or more processes described herein. Device 900 may perform these processes based on processor 904 executing software instructions stored by a computer-readable medium, such as memory 906 and/or storage component 908. A computer-readable medium (e.g., a non-transitory computer-readable medium) is defined herein as a non-transitory memory device. A non-transitory memory device includes memory space located inside of a single physical storage device or memory space spread across multiple physical storage devices.

Software instructions may be read into memory 906 and/or storage component 908 from another computer-readable medium or from another device via communication interface 914. When executed, software instructions stored in memory 906 and/or storage component 908 may cause processor 904 to perform one or more processes described herein. Additionally or alternatively, hardwired circuitry may be used in place of or in combination with software instructions to perform one or more processes described herein. Thus, embodiments or aspects described herein are not limited to any specific combination of hardware circuitry and software.

The number and arrangement of components shown in FIG. 9 are provided as an example. In some non-limiting embodiments or aspects, device 900 may include additional components, fewer components, different components, or differently arranged components than those shown in FIG. 9. Additionally or alternatively, a set of components (e.g., one or more components) of device 900 may perform one or more functions described as being performed by another set of components of device 900.

Although the disclosed subject matter has been described in detail for the purpose of illustration based on what is currently considered to be the most practical and preferred embodiments or aspects, it is to be understood that such detail is solely for that purpose and that the disclosed subject matter is not limited to the disclosed embodiments or aspects, but, on the contrary, is intended to cover modifications and equivalent arrangements that are within the spirit and scope of the appended claims. For example, it is to be understood that the presently disclosed subject matter contemplates that, to the extent possible, one or more features of any embodiment or aspect can be combined with one or more features of any other embodiment.

What is claimed is:

1. A medical device assembly, comprising:
   a first medical device component having at least one first resonant structure, the at least one first resonant structure having a first electromagnetic resonant frequency spectrum; and
   a second medical device component having at least one second resonant structure, the at least one second resonant structure having a second electromagnetic resonant frequency spectrum different than the first electromagnetic resonant frequency spectrum,
   wherein, upon mating of the first medical device component to the second medical device component, the at least one first resonant structure and the at least one second resonant structure combine to have a third electromagnetic resonant frequency spectrum, wherein the third electromagnetic resonant frequency spectrum is different than the first electromagnetic resonant frequency spectrum and the second electromagnetic resonant frequency spectrum,
   wherein, upon interrogation of the first medical device component with a multi-frequency electromagnetic signal, the at least one first resonant structure attenuates at least one first frequency component of the multi-frequency electromagnetic signal corresponding to the first electromagnetic resonant frequency spectrum to form a first attenuated electromagnetic signal,
   wherein, upon interrogation of the second medical device component with the multi-frequency electromagnetic signal, the at least one second resonant structure attenuates at least one second frequency component of the multi-frequency electromagnetic signal corresponding to the second electromagnetic resonant frequency spectrum to form a second attenuated electromagnetic signal, and
   wherein, upon interrogation of the first medical device component mated with the second medical device component with the multi-frequency electromagnetic signal, at least one third frequency component of the multi-frequency electromagnetic signal corresponding to the third electromagnetic resonant frequency spectrum is attenuated to form a third attenuated electromagnetic signal.

2. The medical device assembly of claim 1, wherein the at least one first resonant structure comprises a first spiral resonator, wherein the first electromagnetic resonant frequency spectrum comprises a first natural frequency of the first spiral resonator, wherein the at least one second resonant structure comprises a second spiral resonator, and wherein the second electromagnetic resonant frequency spectrum comprises a second natural frequency of the second spiral resonator.

3. The medical device assembly of claim 2, wherein, upon mating of the first medical device component to the second medical device component, the first spiral resonator and the second spiral resonator are coupled to form a resonant circuit having a third natural frequency, and wherein the third electromagnetic resonant frequency spectrum comprises the third natural frequency of the resonant circuit.

4. The medical device assembly of claim 2, wherein the first spiral resonator comprises a first spiral-shaped metallic conductor adjacent to a first metallic strip of at least one first antenna element of the first medical device component, the first spiral-shaped metallic conductor having a first inductance, a first capacitance, and a first resistance, and wherein the second spiral resonator comprises a second spiral-shaped metallic conductor adjacent to a second metallic strip of at least one second antenna element of the second medical device component, the second spiral-shaped metallic conductor having a second inductance, a second capacitance, and a second resistance, wherein at least one of the first inductance, first capacitance, or first resistance is different than at least one of the second inductance, second capacitance, or second resistance, respectively.

5. The medical device assembly of claim 1, wherein the first medical device component comprises a male luer fitting and the second medical device component comprises a corresponding female luer fitting, and wherein the at least one first resonant structure is disposed with the male luer fitting and the at least one second resonant structure is disposed with the female luer fitting.

6. The medical device assembly of claim 1, wherein the at least one first resonant structure comprises a plurality of first resonant structures, each of the plurality of first resonant structures positioned at a distinct scale marking on the first medical device component, and wherein each of the plurality of first resonant structures comprises a conductive ink.

7. The medical device assembly of claim 1, wherein the first medical device component comprises a first receiving antenna element and a first transmitting antenna element, wherein the first receiving antenna element and the first transmitting antenna element are cross-polarized, wherein the second medical device component comprises a second receiving antenna element and a second transmitting antenna element, and wherein the second receiving antenna element and the second transmitting antenna element are cross-polarized.

8. The medical device assembly of claim 1, wherein the multi-frequency electromagnetic signal is generated by a first generator, and wherein at least one of the first attenuated electromagnetic signal, the second attenuated electromagnetic signal, or the third attenuated electromagnetic signal are detected by a first reader.

9. A system, comprising:
a medical device assembly, comprising:
a first medical device component having at least one first resonant structure, the at least one first resonant structure having a first electromagnetic resonant frequency spectrum; and
a second medical device component having at least one second resonant structure, the at least one second resonant structure having a second electromagnetic resonant frequency spectrum different than the first electromagnetic resonant frequency spectrum,
wherein, upon mating of the first medical device component to the second medical device component, the at least one first resonant structure and the at least one second resonant structure combine to have a third electromagnetic resonant frequency spectrum, wherein the third electromagnetic resonant frequency spectrum is different than the first electromagnetic resonant frequency spectrum and the second electromagnetic resonant frequency spectrum;
at least one generator configured to transmit an interrogation signal to the medical device assembly; and
at least one reader configured to receive at least one reflected signal from the medical device assembly,
wherein the interrogation signal comprises a multi-frequency electromagnetic signal,
wherein, upon interrogation of the first medical device component with the multi-frequency electromagnetic signal, the at least one first resonant structure attenuates at least one first frequency component of the multi-frequency electromagnetic signal corresponding to the first electromagnetic resonant frequency spectrum to form a first attenuated electromagnetic signal,
wherein, upon interrogation of the second medical device component with the multi-frequency electromagnetic signal, the at least one second resonant structure attenuates at least one second frequency component of the multi-frequency electromagnetic signal corresponding to the second electromagnetic resonant frequency spectrum to form a second attenuated electromagnetic signal, and
wherein, upon interrogation of the first medical device component mated with the second medical device component with the multi-frequency electromagnetic signal, at least one third frequency component of the multi-frequency electromagnetic signal corresponding to the third electromagnetic resonant frequency spectrum is attenuated to form a third attenuated electromagnetic signal.

10. The system of 9, wherein the interrogation signal comprises a continuous wave, multi-frequency electromagnetic signal of uniform amplitude and phase.

11. The system of claim 9, wherein the at least one reader further comprises a first communication interface to communicate reflected signal data associated with the reflected signal over a first network, the system further comprising:
at least one server having a second communication interface configured to communicate with the first communication interface of the at least one reader over the first network, wherein the at least one server is configured to receive the reflected signal data over the first network, and wherein the at least one server is configured to store the reflected signal data in a database.

12. The system of claim 9, wherein the at least one reader comprises a plurality of readers, each reader of the plurality of readers at a location within at least one site, wherein the location of each reader of the plurality of readers is different than the location of all other readers of the plurality of readers.

13. The system of claim 12, wherein a location of the medical device assembly is determined based on which reader of the plurality of readers detects the medical device assembly.

14. The system of claim 9, wherein the at least one first resonant structure comprises a first spiral resonator, wherein the first electromagnetic resonant frequency spectrum comprises a first natural frequency of the first spiral resonator, wherein the at least one second resonant structure comprises a second spiral resonator, and wherein the second electromagnetic resonant frequency spectrum comprises a second natural frequency of the second spiral resonator.

15. The system of claim 14, wherein, upon mating of the first medical device component to the second medical device component, the first spiral resonator and the second spiral resonator are coupled to form a resonant circuit having a third natural frequency, and wherein the third electromagnetic resonant frequency spectrum comprises the third natural frequency of the resonant circuit.

16. The system of claim 9, wherein the first medical device component comprises a male luer fitting and the second medical device component comprises a corresponding female luer fitting, and wherein the at least one first resonant structure is disposed with the male luer fitting and the at least one second resonant structure is disposed with the female luer fitting.

17. The system of claim 9, wherein the at least one first resonant structure comprises a plurality of first resonant structures, each of the plurality of first resonant structures positioned at a distinct scale marking on the first medical device component, and wherein each of the plurality of first resonant structures comprises a conductive ink.

18. The system of claim 9, wherein the first medical device component comprises at least one first antenna element, the second medical device component comprises at least one second antenna element, the generator comprises at least one third antenna element, and the reader comprises at least one fourth antenna element, wherein the generator is configured to transmit the interrogation signal with the at least one third antenna element and the reader is configured to receive the reflected signal with the at least one fourth antenna element, wherein the interrogation signal is received by at least one of the at least one first antenna element or the at least one second antenna element, and wherein the reflected signal is transmitted by at least one of the at least one first antenna element or the at least one second antenna element.

19. A method for detecting mating of medical device components, comprising:
providing a first medical device component having at least one first resonant structure, the at least one first resonant structure having a first electromagnetic resonant frequency spectrum;
providing a second medical device component having at least one second resonant structure, the at least one second resonant structure having a second electromagnetic resonant frequency spectrum different than the first electromagnetic resonant frequency spectrum;
mating the first medical device component to the second medical device component to form a medical device assembly, wherein, upon mating, the at least one first resonant structure and the at least one second resonant structure combine to have a third electromagnetic resonant frequency spectrum, the third electromagnetic resonant frequency spectrum being different than the first electromagnetic resonant frequency spectrum and the second electromagnetic resonant frequency spectrum;
interrogating the medical device assembly with an interrogation signal; and
detecting a reflected signal from the medical device assembly,
wherein the interrogation signal comprises a multi-frequency electromagnetic signal,
wherein, upon interrogation of the first medical device component with the multi-frequency electromagnetic signal, the at least one first resonant structure attenuates at least one first frequency component of the multi-frequency electromagnetic signal corresponding to the first electromagnetic resonant frequency spectrum to form a first attenuated electromagnetic signal,
wherein, upon interrogation of the second medical device component with the multi-frequency electromagnetic signal, the at least one second resonant structure attenuates at least one second frequency component of the multi-frequency electromagnetic signal corresponding to the second electromagnetic resonant frequency spectrum to form a second attenuated electromagnetic signal, and
wherein, upon interrogation of the first medical device component mated with the second medical device component with the multi-frequency electromagnetic signal, at least one third frequency component of the multi-frequency electromagnetic signal corresponding to the third electromagnetic resonant frequency spectrum is attenuated to form a third attenuated electromagnetic signal.

20. The method of claim 19, further comprising storing reflected signal data associated with the reflected signal in a database.

21. The method of claim 19, wherein detecting the reflected signal comprises detecting the reflected signal with a reader, wherein the reader is one of a plurality of readers, each reader of the plurality of readers at a location within at least one site, the method further comprising:
determining a location of the medical device assembly based on the location of the reader.

22. The method of claim 19, wherein the at least one first resonant structure comprises a first spiral resonator, wherein the first electromagnetic resonant frequency spectrum comprises a first natural frequency of the first spiral resonator, wherein the at least one second resonant structure comprises a second spiral resonator, wherein the second electromagnetic resonant frequency spectrum comprises a second natural frequency of the second spiral resonator, wherein, upon mating of the first medical device component to the second medical device component, the first spiral resonator and the second spiral resonator are coupled to form a resonant circuit having a third natural frequency, and wherein the third electromagnetic resonant frequency spectrum comprises the third natural frequency of the resonant circuit.

23. The method of claim 19, wherein the first medical device component comprises a male luer fitting and the second medical device component comprises a corresponding female luer fitting, and wherein the at least one first resonant structure is disposed with the male luer fitting and the at least one second resonant structure is disposed with the female luer fitting.

24. The method of claim 19, wherein the at least one first resonant structure comprises a plurality of first resonant structures, each of the plurality of first resonant structures positioned at a distinct scale marking on the first medical device component, and wherein each of the plurality of first resonant structures comprises a conductive ink.

* * * * *

UNITED STATES PATENT AND TRADEMARK OFFICE
CERTIFICATE OF CORRECTION

PATENT NO. : 11,992,374 B2
APPLICATION NO. : 17/922840
DATED : May 28, 2024
INVENTOR(S) : Noel Titus Page 1 of 1

It is certified that error appears in the above-identified patent and that said Letters Patent is hereby corrected as shown below:

In the Claims

Column 50, Line 5, Claim 10, after "of" insert -- claim --

Signed and Sealed this
Seventh Day of January, 2025

Derrick Brent
*Acting Director of the United States Patent and Trademark Office*